United States Patent
Hussain et al.

(10) Patent No.: US 11,858,878 B2
(45) Date of Patent: Jan. 2, 2024

(54) GEMINI SURFACTANT COMPOSITION AND METHOD FOR TREATING SUBTERRANEAN ROCK

(71) Applicant: KING FAHD UNIVERSITY OF PETROLEUM AND MINERALS, Dhahran (SA)

(72) Inventors: Syed M. Shakil Hussain, Dhahran (SA); Muhammad Shahzad Kamal, Dhahran (SA); Abdullah S. Sultan, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 94 days.

(21) Appl. No.: 18/052,231

(22) Filed: Nov. 3, 2022

(65) Prior Publication Data
US 2023/0132932 A1 May 4, 2023

Related U.S. Application Data

(63) Continuation of application No. 16/281,849, filed on Feb. 21, 2019, now Pat. No. 11,512,045.

(60) Provisional application No. 62/633,314, filed on Feb. 21, 2018.

(51) Int. Cl.
| | |
|---|---|
| *C07C 237/16* | (2006.01) |
| *C09K 8/584* | (2006.01) |
| *C07C 381/06* | (2006.01) |
| *C11D 1/00* | (2006.01) |
| *C07C 233/36* | (2006.01) |
| *C07C 233/38* | (2006.01) |

(Continued)

(52) U.S. Cl.
CPC .......... *C07C 237/16* (2013.01); *C07C 233/36* (2013.01); *C07C 233/38* (2013.01); *C07C 381/06* (2013.01); *C09K 8/584* (2013.01); *C11D 1/00* (2013.01); *C07C 231/02* (2013.01); *C09K 2208/30* (2013.01); *E21B 43/16* (2013.01)

(58) Field of Classification Search
None
See application file for complete search history.

(56) References Cited

U.S. PATENT DOCUMENTS

| | | |
|---|---|---|
| 2,991,290 A | 7/1961 | Shapiro et al. |
| 5,118,717 A | 6/1992 | Hodgdon et al. |
| 6,989,149 B2 | 1/2006 | Glenn, Jr. |

(Continued)

OTHER PUBLICATIONS

Seymour L. Shapiro, et al., "Aminoalkylamides and Oxazolidinediones", Journal of the American Chemical Society, vol. 81, No. 12, Jun. 1959, pp. 3083-3088 (Abstract only).

(Continued)

*Primary Examiner* — John J Figueroa
(74) *Attorney, Agent, or Firm* — Oblon, McClelland, Maier & Neustadt, L.L.P.

(57) ABSTRACT

The invention concerns synthesized amido-amine-based cationic gemini surfactants with flexible and rigid spacers and different hydrophobic. These gemini surfactants were prepared by modified procedure through amidation of long chain carboxylic acids using 3-(dimethylamino)-1-propylamine followed by treatment with halohydrocarbons and showed excellent thermal stability and surface properties useful for various oilfield applications such as enhanced oil recovery.

18 Claims, 11 Drawing Sheets

(51) Int. Cl.
  *C07C 231/02*  (2006.01)
  *E21B 43/16*  (2006.01)

(56) References Cited

U.S. PATENT DOCUMENTS

| | | | |
|---|---|---|---|
| 8,222,455 B2 | 7/2012 | Knox | |
| 9,074,123 B2* | 7/2015 | Hernandez | C07C 229/12 |
| 2004/0235677 A1 | 11/2004 | Nguyen | |
| 2007/0141007 A1 | 6/2007 | Glynn, Jr. | |
| 2009/0259062 A1 | 10/2009 | Wang | |
| 2011/0071056 A1* | 3/2011 | Saini | C09K 8/035 |
| | | | 507/131 |
| 2012/0270758 A1* | 10/2012 | Saini | C09K 8/035 |
| | | | 507/131 |
| 2016/0272875 A1* | 9/2016 | Ghumare | C09K 8/035 |
| 2017/0081582 A1* | 3/2017 | Ghumare | C09K 8/74 |
| 2017/0304160 A1 | 10/2017 | Nagamatsu | |
| 2018/0078480 A1 | 3/2018 | Adam | |
| 2018/0311140 A1 | 11/2018 | Perner | |

OTHER PUBLICATIONS

S. M. Shakil Hussain, et al., "Synthesis and Evaluation of Novel Amido-Amine Cationic Gemini Surfactants Containing Flexible and Rigid Spacers", Journal of Surfactants and Detergents, vol. 20, No. 4, 2017, pp. 777-788.

Muhammad Shahzad Kamal, et al., "Impact of Spacer and Hydrophobic Tail on Interfacial and Rheological Properties of Cationic Amido-Amine Gemini Surfactants for EOR Application", Physical Chemistry, Tenside Surf. Det., vol. 55, Issue 6, Nov. 2018, pp. 1-7.

* cited by examiner

Fig. 1A
Fig. 1B
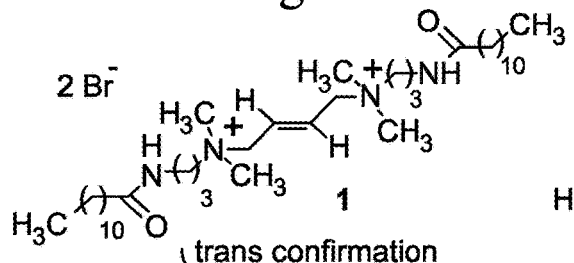
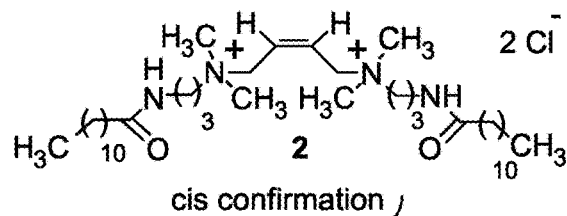
trans confirmation
cis confirmation
Fig. 1C
Fig. 1D
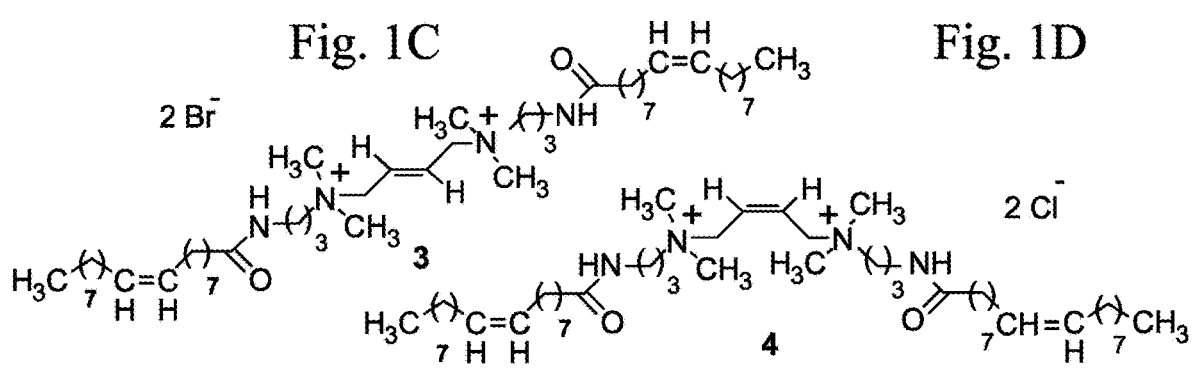
trans confirmation
cis confirmation
Fig. 1E
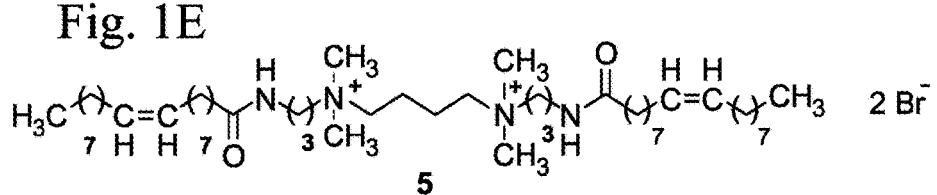
Fig. 1F
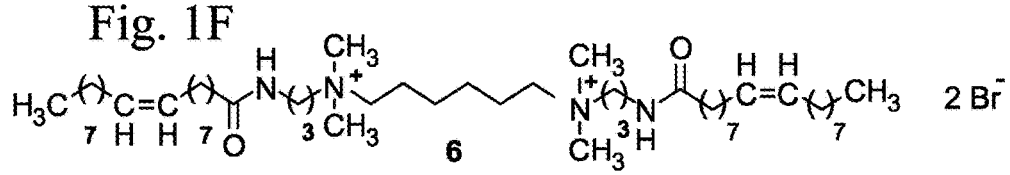

Scheme 1

GEMINI SURFACTANT COMPOSITION AND METHOD FOR TREATING SUBTERRANEAN ROCK

CROSS-REFERENCE TO RELATED APPLICATIONS

The present application is a Continuation of U.S. application Ser. No. 16/281,849, now allowed, having a filing date of Feb. 21, 2019 which is based on, and claims the benefit of priority to, U.S. Provisional Application No. 62/633,314, having a filing date of Feb. 21, 2018, the entire contents of which are incorporated herein by reference.

BACKGROUND OF THE INVENTION

Field of the Invention

The invention falls within the fields of petrochemistry and surfactant chemistry, especially as directed to gemini (dimeric) surfactants which contain two hydrophilic head groups and two hydrophobic groups.

Description of Related Art

Surfactants have been widely applied in various oilfield applications including in drilling mud, and for stimulation, completion, and enhanced oil recovery; Sheng J J (2015) *Status of surfactant EOR technology*. Petroleum 1 (2):97-105. doi:http://dx.doi.org/10.1016/j.petlm.2015.07.003, incorporated herein by reference in its entirety.

The primary job of surfactants in oilfield applications is interfacial tension (IFT) reduction and for alteration of wettability; however, they also act as wetting agents and emulsifiers; Sheng J J (2013) *Comparison of the effects of wettability alteration and IFT reduction on oil recovery in carbonate reservoirs*. Asia-Pacific Journal of Chemical Engineering 8 (1):154-161; Kamal M S, Hussain S S, Sultan A S (2016) *Development of Novel Amidosulfobetaine Surfactant-Polymer Systems for EOR Applications*. J Surfactants Deterg 19 (5):989-997; Kamal M S, Sultan A S, Hussein I A (2015) *Screening of amphoteric and anionic surfactants for cEOR applications using a novel approach*. Colloid Surface A 476:17-23; Al-Amodi A O, Al-Mubaiyedh U A, Sultan A S, Kamal M S, Hussein I A (2016) *Novel fluorinated surfactants for enhanced oil recovery in carbonate reservoirs*. The Canadian Journal of Chemical Engineering 94 (3):454-460; Musselman S W, Chander S (2002) *Wetting and adsorption of acetylenic diol based nonionic surfactants on heterogeneous surfaces*. Colloids and Surfaces A: Physicochemical and Engineering Aspects 206 (1-3):497-513. doi:http://dx.doi.org/10.1016/S0927-7757(02)00055-9; and Ebrahimpour B, Yamini Y, Moradi M (2012) *Application of an ionic surfactant as a carrier and emulsifier agent for the microextraction of fluoroquinolones*. Journal of Pharmaceutical and Biomedical Analysis 66:264-270. doi:http://_dx.doi.org/10.1016/j.jpba.2012.03.028, each incorporated herein by reference in their entirety.

Gemini surfactants are composed of more than one hydrophobic tail and head group joined through spacer; Hait S, Moulik S (2002) *Gemini surfactants: a distinct class of self-assembling molecules*. Current Science Bangalore—82 (9):1101-1111; and Kamal M S (2016) *A review of Gemini surfactants: potential application in enhanced oil recovery*. Journal of Surfactants and Detergents 19 (2):223-236, each incorporated herein by reference in their entirety.

Due to their unique structure gemini surfactants are superior to conventional single head single tail surfactants in terms of higher efficiency in IFT reduction, lower critical micelle concentrations (cmc), solubility, viscoelastic behavior, gel formation, wetting properties, and shear thickening; Pozniak B P, Kuliszewska E (2014) *Intracluster reactions in negatively charged aggregates of diquaternary amines Gemini surfactants with bromide and formate counterions*. International Journal of Mass Spectrometry 359:44-54. doi: http://dx.doi.org/10.1016/j.ijms.2013.12.016; Alimohammadi M H, Javadian S, Gharibi H, reza Tehrani-Bagha A, Alavijeh M R, Kakaei K (2012) *Aggregation behavior and intermicellar interactions of cationic Gemini surfactants: Effects of alkyl chain, spacer lengths and temperature*. The Journal of Chemical Thermodynamics 44 (1):107-115; and Deng M, Li J, Liu J, Ma X, Wang Y (2010) *Abnormal interfacial tension behavior of alkanediyl-α,ω-bis(dodecyldimethylammonium bromide) Gemini surfactants*. Colloids and Surfaces A: Physicochemical and Engineering Aspects 356 (1-3):97-103. doi:http://dx.doi.org/10.1016/j.colsurfa.2009.12.032, each incorporated herein by reference in their entirety.

In the past decades, many reports appeared in literature and focused on the study of cationic gemini surfactants containing a quaternary ammonium head group with different tail and spacer lengths; Shukla D, Tyagi V (2006) *Cationic Gemini surfactants: a review*. Journal of Oleo Science 55 (8):381-390, incorporated herein by reference in its entirety. The cationic gemini surfactants are extensively applied in medicine, household, biotechnology, pharmacy, oilfield, and other industries; Kumar N, Tyagi R (2014) *Industrial applications of dimeric surfactants: a review*. J Dispersion Sci Technol 35 (2):205-214; Gerba C P (2015) *Quaternary ammonium biocides: efficacy in application*. Applied and Environmental Microbiology 81 (2):464-469; Akram M, Bhat I A, Anwar S, Kabir ud D *Biophysical analysis of novel oxy-diester hybrid cationic Gemini surfactants (Cm-E2O-Cm) with xanthine oxidase (XO)*. Process Biochemistry. doi:http://_dx.doi.org/10.1016/j.procbio.2016.05.014; Madunić-Čačić D, Sak-Bosnar M, Galović O, Sakač N, Matešić-Puač R (2008), *Determination of cationic surfactants in pharmaceutical disinfectants using a new sensitive potentiometric sensor*. Talanta 76 (2):259-264. doi:http://dx.doi.org/10.1016/j.talanta.2008.02.023; Ma K, Cui L, Dong Y, Wang T, Da C, Hirasaki G J, Biswal S L (2013) *Adsorption of cationic and anionic surfactants on natural and synthetic carbonate materials*. Journal of Colloid and Interface Science 408:164-172. doi:http://dx-.doi.org/10.1016/j.jcis.2013.07.006; and Abd El-Lateef H M, Abo-Riya M A, Tantawy A H (2016) *Empirical and quantum chemical studies on the corrosion inhibition performance of some novel synthesized cationic Gemini surfactants on carbon steel pipelines in acid pickling processes*. Corrosion Science 108:94-110. doi:http://_dx.doi.org/10.1016/j.corsci.2016.03.004, each incorporated herein by reference in their entirety.

The salient features of many ammonium-based cationic gemini surfactants include economic feasibility, environmentally friendliness, excellent water solubility, and utility for various oil field applications; Negm N A, Aiad I A (2007) *Synthesis and characterization of multifunctional surfactants in oil-field protection applications*. Journal of Surfactants and Detergents 10 (2):87-92 and U.S. Patent Publication 20170369759 describes anionic dimer surfactant compositions for enhanced oil recovery (both incorporated by reference).

Cationic gemini surfactants may be useful for hydrocarbon recovery from carbonate reservoirs where anionic surfactants are avoided because of high adsorption on carbonate rock. Carbonate reservoirs represent almost 60% of the world's oil. Cationic surfactants change the wettability of carbonate rocks from oil-wet to water wet resulting in enhanced oil production; Joonaki E, Erfani Gahrooei H R, Ghanaatian S (2016) *Experimental study on adsorption and wettability alteration aspects of a new chemical using for enhanced oil recovery in carbonate oil reservoirs*. Journal of Unconventional Oil and Gas Resources 15:11-21. doi:http://dx.doi.org/10.1016/j.juogr.2016.05.001; and Sheng J J (2011) Chapter 7—*Surfactant Flooding*. In: Modern Chemical Enhanced Oil Recovery. Gulf Professional Publishing, Boston, pp 239-335. doi:http://dx.doi.org/10.1016/B978-1-85617-745-0.00007-3, each incorporated herein by reference in their entirety.

Gemini surfactants aggregate in aqueous media to form micelles and the size and the shapes of such micelles mainly depend on the spacer group; Manne S, Schaffer T, Huo Q, Hansma P, Morse D, Stucky G, Aksay I (1997) *Gemini surfactants at solid-liquid interfaces: control of interfacial aggregate geometry*. Langmuir 13 (24):6382-6387, incorporated herein by reference in its entirety. The nature and the length of spacer found to be the most significant parameter determining the surface properties of gemini surfactants; Zana R (2002) *Dimeric (Gemini) surfactants: effect of the spacer group on the association behavior in aqueous solution*. J Colloid Interface Sci 248 (2):203-220. doi:10.1006/jcis.2001.8104; and Parikh K, Mistry B, Jana S, Gupta S, Devkar R V, Kumar S (2015) *Physico-biochemical studies on cationic Gemini surfactants: Role of spacer*. Journal of Molecular Liquids 206:19-28. doi:http://dx.doi.org/10.1016/j.molliq.2015.01.055, each incorporated herein by reference in their entirety.

The spacer can be flexible (hydrophobic methylene group or hydrophilic polyethylene oxide group) or it can be rigid with double bond, triple bond, or benzene ring; Du X, Lu Y, Li L, Wang J, Yang Z (2006) *Synthesis and unusual properties of novel alkylbenzene sulfonate Gemini surfactants*. Colloids and Surfaces A: Physicochemical and Engineering Aspects 290 (1):132-137; Bendjeriou-Sedjerari A, Derrien G, Charnay C, Zajac J, De Menorval L C, Lindheimer M (2009) *Contribution of 1H NMR to the investigation of the adsorption of cationic Gemini surfactants with oligooxyethylene spacer group onto silica*. Journal of Colloid and Interface Science 331 (2):281-287. doi:http://dx.doi.org/10.1016/j.jcis.2008.12.007; Zhang Z, Wang H, Zheng P, Shen W (2013) *Effect of spacer rigidity on the aggregations of ester containing Gemini surfactants in aqueous solutions: a study of density and fluorescence*. Colloids and Surfaces A: Physicochemical and Engineering Aspects 421:193-200; Menger F, Keiper J, Azov V (2000) *Gemini surfactants with acetylenic spacers*. Langmuir 16 (5):2062-2067; and Zhu D-Y, Cheng F, Chen Y, Jiang S-C (2012) *Preparation, characterization and properties of anionic Gemini surfactants with long rigid or semi-rigid spacers*. Colloid Surface A 397:1-7, each incorporated herein by reference in their entirety.

Polyether or phenyl moieties may be introduced to maximize or minimize the spacer rigidity; Mivehi L, Bordes R, Holmberg K (2011) *Adsorption of cationic Gemini surfactants at solid surfaces studied by QCM-D and SPR: effect of the rigidity of the spacer*. Langmuir 27 (12):7549-7557, incorporated herein by reference in its entirety. However, such polyether and phenyl moieties can also alter the spacer chain length and hydrophobicity. Therefore, the surfactants' aggregation morphologies could be affected by the spacer rigidity, length, hydrophobicity, and $\pi$-$\pi$ stacking interactions between benzene rings; Zhang Z, Zheng P, Guo Y, Yang Y, Chen Z, Wang X, An X, Shen W (2012); *The effect of the spacer rigidity on the aggregation behavior of two ester-containing Gemini surfactants*. Journal of Colloid and Interface Science 379 (1):64-71, incorporated herein by reference in its entirety.

In view of the above, the inventors sought to design new cationic gemini surfactants that exhibit excellent temperature stability and which have superior functional properties such as lower cmc, lower IFT, and better rheological properties for oil field and other industrial or commercial applications.

BRIEF SUMMARY OF THE INVENTION

Among its other aspects the invention is directed to six families of amido-amine-based cationic gemini surfactants containing gemini surfactants (1), (2), (3), (4), (5) and (6), to compositions containing them, and to methods for their production and use. Commercial and industrial applications include their use as agents for increasing recovery of crude oil or other hydrocarbons from a subterranean hydrocarbon-containing formation or in a hydrocarbon-containing subterranean reservoir formed by hydraulic fracturing or "fracking". Typically, the compositions are thermally stable when subjected to underground conditions including temperatures at or above 50° C. to 200° C. and/or water sources having high total dissolved mineral, metal or salt solids.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 1A-1B depict the structures of gemini surfactant (1) having a spacer in trans conformation with the nitrogen atoms on each end and gemini surfactant (2) having a spacer in a cis conformation.

FIGS. 1C-1D depict the structures of gemini surfactant (3) having a spacer in trans conformation and gemini surfactant (4) having a spacer in a cis conformation.

FIGS. 1E and 1F structures of gemini surfactants (5) and (6) which each have an alkyl spacer.

DETAILED DESCRIPTION OF THE INVENTION

Figure 2:
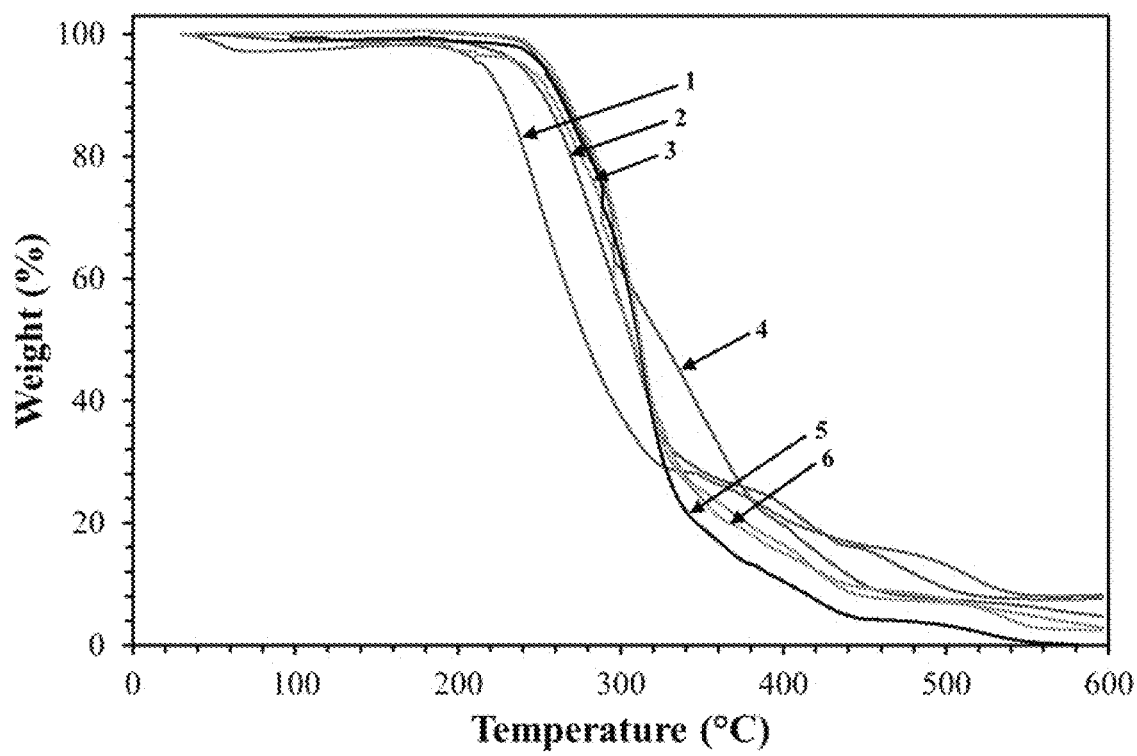
FIG. 2. TGA curves of the gemini surfactants (1)-(6) under nitrogen atmosphere.

The invention concerns a genus of synthesized amido-amine-based cationic gemini surfactants with flexible or rigid central spacers between nitrogen-atom-containing head groups and hydrophobic tails. These gemini surfactants were prepared by modified procedure through amidation of long chain carboxylic acids followed by treatment of halohydrocarbons as exemplified by Scheme 1 below.

The effects of a gemini surfactant containing either a trans or cis conformation of the spacer double bond on critical micelle concentration, surface tension reduction, and thermal stabilities were determined. The short-term thermal stability of the gemini surfactants was assessed using thermogravimetric analysis (TGA) and the long-term thermal stability was examined by a unique approach based on structure characterization techniques including NMR ($^1$H and $^{13}$C) and FTIR analysis. TGA results exhibited excellent short-term thermal stability and no structure degradation was observed up to 200° C. Structural characterization revealed impressive long-term thermal stability of the gemini surfactants with no structure decomposition after exposing them to 90° C. for 10 days. The critical micelle concentration results of gemini surfactants were found to be in the range of $0.77 \times 10^{-4}$ mol L$^{-1}$ to $3.61 \times 10^{-4}$ mol L$^{-1}$ and corresponding surface tension ($\gamma_{cmc}$) results were ranged from 30.34 mN m$^{-1}$ to 38.12 mN m$^{-1}$. The surface properties of the trans conformation of spacer double bond found to be predominant compared to cis conformation. The gemini surfactants showed excellent thermal stability and surface properties which made them good candidates for various oilfield applications such as enhanced oil recovery.

The gemini surfactants of the invention generally conform to Formula (I):

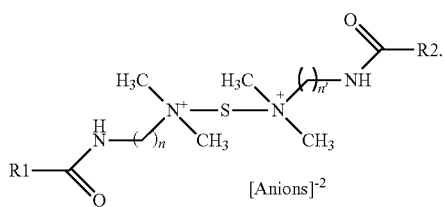

wherein:
R1 and R2 are $C_8$-$C_{30}$ alkyl or $C_{10}$-$C_{30}$ alkenyl, preferably $C_{12}$-$C_{18}$ alkyl or $C_{12}$-$C_{18}$ alkenyl,
S is a linear $C_4$, $C_6$ or $C_8$ alkylene or linear $C_4$, $C_6$ or $C_8$ alkenylene spacer, and
n and n' are $C_2$-$C_5$ alkylene. The substituents on either side of the spacer S may be linked to it in cis or in trans.

Six exemplary gemini surfactants according to Formula (I) were synthesized and designated amido-amine-based cationic gemini surfactants (1)-(6) These exemplary gemini surfactants conforming to Formula (I) were designed with different spacer groups and different hydrophobic tails and allowed the inventors to assess and compare the functional properties of gemini surfactants of Formula (I). The inventors determined the effects of spacer length, spacer rigidity, trans and cis conformation of the spacer double bond, and hydrophobic tail length with regard to thermal stability, surface tension, and other functional properties.

Gemini surfactants (1) and (3) and gemini surfactants (2) and (4) were designed to have similar trans- or cis-linked spacer groups but to differ in their hydrophobic tail groups.

Three amido-amine based cationic gemini surfactants (3)-(5) were produced which a similar hydrophobic tail group but which had differed with regard to rigidity and flexibility of the spacer. For engineering these surfactants, two spacer lengths $C_4$ and $C_6$ were selected to determine whether these lengths would produce noticeable changes in surfactant properties; Laschewsky A, Lunkenheimer K, Rakotoaly R H, Wattebled L (2005) *Spacer effects in dimeric cationic surfactants*. Colloid Polym. Sci. 283 (5):469-479, incorporated herein by reference in its entirety. A dodecyl group was selected as a hydrophobic tail to determine whether it would deliver useful functional properties to a gemini surfactant; and an olea tail was chosen to determine whether it would confer a decrease critical micelle concentration ("cms") with an increase of the chain length; Huang Z, Zhong H, Wang S, Xia L, Zou W, Liu G (2014) *Investigations on reverse cationic flotation of iron ore by using a Gemini surfactant: Ethane-1,2-bis(dimethyl-dodecyl-ammonium bromide)*. Chemical Engineering Journal 257:218-228. doi:http://dx.doi.org/10.1016/j.cej.2014.07.057; and Lee M-T, Vishnyakov A, Neimark A V (2013) *Calculations of critical micelle concentration by dissipative particle dynamics simulations: the role of chain rigidity*, Journal of Physical Chemistry B 117 (35):10304-10310, each incorporated herein by reference in their entirety.

The gemini surfactants of the invention contain two hydrophobic tails which may be derived from saturated or unsaturated fatty acid precursors. These tails comprise R1 and R2 in Formula (I). R1 and R2, may be the same or different, preferably the same, and can comprise $C_8$ to $C_{30}$ alkyl or $C_8$ to $C_{30}$ alkenyl. In some embodiments R1 and R2 comprise $C_8$, $C_9$, $C_{10}$, $C_{11}$, $C_{12}$, $C_{13}$, $C_{14}$, $C_{15}$ or $C_{16}$ alkyl or alkenyl and will not exceed $C_{16}$. In other embodiments R1 and R2 may comprise $C_{17}$-$C_{27}$ alkyl or $C_{17}$-$C_{27}$ alkenyl. Preferably, the fatty acid precursors of R1 and R2 are unbranched.

Examples of saturated fatty acid substrates for production of R1 and R2 (e.g., by steps similar to those described by Scheme 1) include, but are not limited to, caprylic acid, capric acid, lauric acid, myristic acid, palmitic acid, stearic acid, arachidic acid, behenic acid, lignoceric acid and cerotic acid.

Examples of unsaturated fatty acid substrates for production of R1 and R2 include, but are not limited to, myristoleic acid, palmitoleic acid, sapienic acid, oleic acid, elaidic acid, vaccenic acid, linoleic acid, linoelaidic acid, alpha-linolenic acid, arachidonic acid, eicosapentaenoic acid, erucic acid, and docosahexaenoic acid.

As shown herein for gemini surfactants (1)-(4), 3-(dimethylamino)-1-propylamine (9) is used to provide a linkage of three carbons between the nitrogen atoms in the polar head groups separated by the central spacers. In other embodiments, shorter or longer analogs of (9) can be used to adjust spacing between the nitrogen atoms, for example, compounds of the formula, $H_2N—(CH_2)_m—N(CH_3)_2$, where m is 2-5. Similarly, the central spacer may be produced using substrates such as halogen-$(CH_2)_o$-halogen where o is 4-8 or with halogen-alkenyl-halogen, wherein the alkenyl has 4 to 8 carbon atoms.

Compositions containing Gemini surfactants. The gemini surfactants of the invention may be added to one or more fluids used to recover petroleum, gas or other hydrocarbons, for example, to an injected fluid, to produced water, injected fluid or to flowback water. These compositions may be prepared as emulsions and may include ingredients besides water and a gemini surfactant.

Produced water describes water that is produced as a byproduct along with the oil and gas. Oil and gas reservoirs often have water as well as hydrocarbons, sometimes in a zone that lies under the hydrocarbons, and sometimes in the same zone with the oil and gas.

Injected fluid/Fracturing fluid. Fracturing or "fracking" fluid is typically primarily water containing sand or other proppants suspended with a thickening agent. It is usually injected at high pressure into a wellbore to create cracks in the deep-rock formations through which natural gas, petroleum, and brine can flow more freely. When the hydraulic pressure is removed from the well, small grains of hydraulic fracturing proppants, such as sand, silica sand, resin-coated sand, or aluminum oxide, bauxite, or man-made ceramics, hold the fractures open.

Flow back water. During hydrocarbon recovery procedures like fracking less than half of injected water may be recovered as flowback or later production brine and in many cases recovery is <30%. As a fracturing fluid flows back through the well it may contain spent fluids and dissolved constituents such as minerals and brine waters.

Gemini surfactant applications. The gemini surfactants and compositions of the invention may be used in various methods in the fields of oil drilling and petrochemistry such as for increased recovery of crude oil or other hydrocarbons from a subterranean hydrocarbon-containing formation or during hydraulic fracturing. The compositions are thermally stable when subjected to underground conditions including temperatures of about 70, 80, 90, 100, 110, 120 130, 140, 150, 160, 170, 180, 190, 200 and >200° C. and/or to water sources having a high content of dissolved solids, such as water with greater than 500, 1,000, 2,000, 10,000, 20,000, 50,000 or 100,000 ppm dissolved salts, metals and/or minerals. Preferably, the compositions are stable for periods of at least 72 hours at a temperature of 100° C. such that the amount of the gemini surfactants (1)-(6) remains at least 95%, preferably 98%, 99% or 99.5% of the starting amount. The cmc of gemini surfactants (1)-(6) preferably ranges from $1.0 \times 10^{-4}$ mol/L to $5 \times 10^{-4}$ mol/L, preferably more from $0.77 \times 10^{-4}$ mol/L to $3.61 \times 10^{-4}$ for improved oil recovery.

Injection of a gemini surfactant containing composition of the invention into an oil-containing reservoir, causes rock contacted by the composition to change from oil-wettable to water-wettable rock. However, the components of the compositions exhibit a low tendency to adsorb onto the rock and also inhibit formation of emulsions in underground fracturing fluid flows.

The compositions substantially increase the yield of hydrocarbons from underground reservoirs when injected and are particularly useful for increasing yield of hydrocarbons in reservoirs comprising high temperature water sources, high total dissolved solids water sources, or high temperature/high total dissolved solids water sources including from tight shale reservoirs.

Other applications include use of the gemini surfactants as corrosion inhibitors or biocides. Methods of use include those contacting one or more gemini surfactants with metal surfaces of tools or drilling equipment exposed to corrosive fluids in amounts sufficient to inhibit or prevent corrosion and methods of contacting tools or drilling equipment with a concentration of gemini surfactant sufficient to prevent, inhibit or remove biofilms. Suitable concentrations of a gemini surfactant for these purposes may range from 0.01, 0.02, 0.05, 0.1, 0.2, 0.5, 1 or >1 mM or any intermediate values within this range. The gemini surfactants of the invention may also be used as demulsifiers for breaking water-in-crude oil emulsions, for example, to increase water separation efficiency or decrease water separation time from crude oil emulsions. The gemini surfactants of the invention may also be used a defoaming or emulsifying agents in a variety of different products include those used to provide coatings or inks for paper, wood, plastic, ceramics, glass or metals. They may be incorporated into architectural coatings; printing inks, overprint varnishes and fountain solutions; adhesives, dye and pigment synthesis, pigment grinding, oil and gas processing, cleaning products, semiconductor cleaning and processing fluids, metalworking fluids, cements, mortars and grouts, and personal care products, such as soaps, shampoos, body washes, lotions, and other cosmetics, in amounts ranging from 0.01, 0.02, 0.05, 0.1, 0.2, 0.5, 1 or >1 mM or any intermediate value within this range.

Embodiments of the invention include, but are not limited to those described below.

One embodiment of the invention is a gemini surfactant described by formula (I):

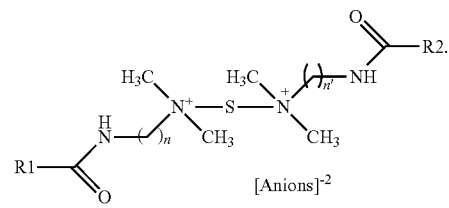

wherein:

R1 and R2 are $C_8$-$C_{30}$ alkyl or $C_{10}$-$C_{30}$ alkenyl, preferably $C_{12}$-$C_{18}$ alkyl or $C_{12}$-$C_{18}$ alkenyl, S is a $C_4$, $C_6$ or $C_8$ linear alkylene or $C_4$, $C_6$ or $C_8$ linear alkenylene spacer bonded on each end to a nitrogen atom, and n and n' are $C_2$-$C_5$ alkylene.

In some embodiments R1 and R2 may be the same or different. In some embodiments, R1 and R2 may contain cis or trans double bonds to other portions of the gemini surfactant structure.

The gemini surfactants of the invention comprise counterions to the charged nitrogen groups. These are typically, halide ions, such as two bromide anions or two chloride anions. However, in other embodiments, they may contain one or more or a mixture of different anions, such as other halogen anions like F$^-$, Cl$^-$, I$^-$ or As$^-$ or other anions such as NO$_3^-$, SO$_4^{2-}$, alkylsulfate such as methyl or ethylsulfate, alkylphosphate such as methylphosphate, and the like.

Mixtures of 2, 3, 4, 5 or 6 or more of these gemini surfactants may be made.

Advantageously, a gemini surfactant according to this embodiment is selected from the group consisting of gemini surfactants (1), (2), (3), (4), (5), and (6) comprising the structures depicted below and anion(s) having a total charge of −2, for example, comprising two bromide or two chloride anions:

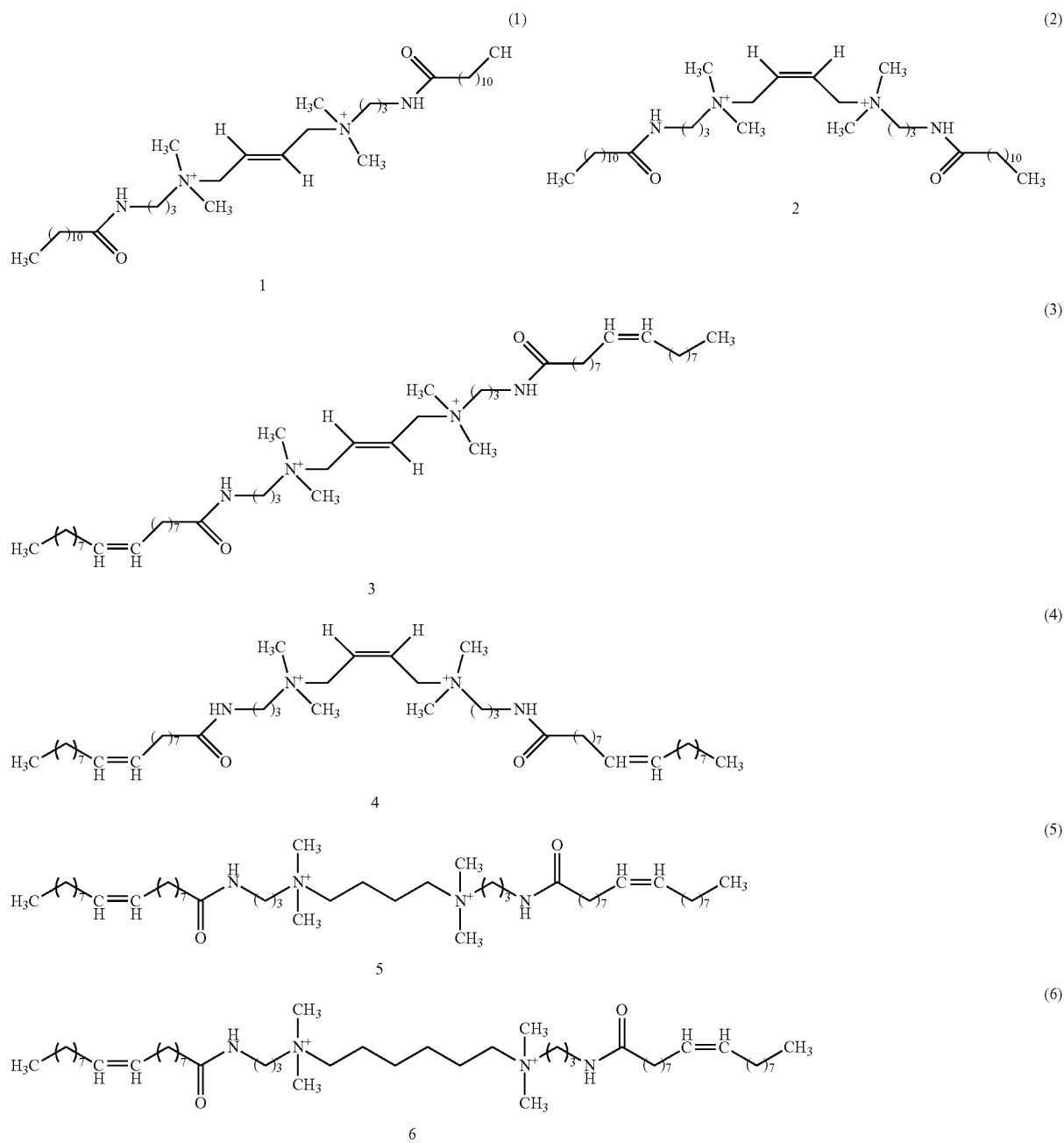

The gemini surfactants of the invention comprise counter anions having a total charge of −2. These counterions include halides such as Br⁻, F⁻, Cl⁻, I⁻ or As⁻ as well as other anions such as $NO_3^-$, $SO_4^{2-}$, alkylsulfate such as methyl or ethylsulfate, alkylphosphate such as methylphosphate, and the like. As synthesized in Scheme 1 gemini surfactants (1), (3), (5) and (6) contain two bromide anions and gemini surfactants (2) and (4) contain two chloride anions.

A gemini surfactant composition may contain other surfactants such as monomeric cationic, monomeric nonionic, or monomeric anionic surfactants conventionally used in petroleum recovery. Cationic surfactants used for petroleum recovery include cetyl trimethyl ammonium bromide (CTAB), coco alkyl trimethyl ammonium chloride, stearyl trimethyl ammonium chloride, dodecyl trimethyl ammonium bromide (DTAB), ethoxylated alkyl amine, and cationic surfactants with quaternary ammonium surfactants having an amide linkage such as: Other conventional cationic, nonionic and anionic surfactants that may be admixed with or used in conjunction with a gemini surfactant according to the invention includes those described by Raffa, et al., J. Petroleum Sci. 145:723-733 (2016), or by Negin, et al., Petroleum 3(2): 197-211 (2017), which are incorporated by reference.

Such a composition can have a weight ratio of the at least one gemini surfactant to the monomeric or non-dimeric surfactant of about 3:1, 2:1, 1:1, 1:2 to 1:3 (or any intermediate ratio within this range).

A gemini surfactant composition may contain a demulsifier to prevent emulsion formation within the subterranean reservoir. When injected into a well the compositions containing the gemini surfactants are preferably not in the form of an emulsion and instead in the form of a single phase organic or aqueous solution.

When present, a demulsifier may be selected from the group comprising, consisting essentially of, or consisting of polyethylenimine alkoxylates, alkoxylated alkylphenol formaldehyde resins, alkoxylated amine-modified alkylphenol formaldehyde resins, ethylene oxide/propylene oxide copolymers, crosslinked ethylene oxide/propylene oxide copolymers, and mixtures of these. When employed in a composition for petroleum recovery, the demulsifier may be present in an amount ranging from 0.01, 0.02, 0.05, 0.1, 0.2, 0.5, 1, 2, 3, 4, 5 or >5 wt % based on the total weight of the composition for injection.

In some embodiments a composition containing a gemini surfactant of the invention will also include coupling agent. A coupling agent may be selected from the group consisting of one or more of a linear, branched, or cyclic aliphatic alcohol having 1, 2, 3, 4, 5 to 6 carbon atoms, diols having 1, 2, 3, 4, 5 to 6 carbon atoms, alkyl ethers of alkylene glycols wherein the alkyl moiety has 1, 2, 3, 4, 5 to 6 carbon atoms, polyalkylene glycols, and mixtures of two or more thereof. When employed in a composition for petroleum recovery, the coupling agent may be present in an amount ranging from 0.001, 0.002, 0.005, 0.01, 0.02, 0.05, 0.1, 0.2, 0.3, 0.4, 0.5 or >0.5 wt % based on the total weight of the composition for injection. This range includes all intermediate values and subranges.

In some embodiments, the compositions further include one or more additives, wherein the additives are selected from clay stabilizers, corrosion inhibitors, scale inhibitors, viscosifying agents, solvents, flow back aids, friction reducers, proppants (e.g. silica sand, aluminum oxide), biocides, or mixtures thereof. Preferably, the gemini surfactants are injected as a single component fluid into wells without any co-surfactant or co-solvent.

During use in oil field operations, a gemini surfactant is admixed with water such as produced water or water having a high content of dissolved solids. In some embodiments the water source is a high temperature water source, a high total dissolved solids water source, or a high temperature, high total dissolved solids water source, such as water with greater than 500, 1,000, 2,000, 10,000, 20,000, 50,000 or 100,000 ppm dissolved solids. This range includes all intermediate values and subranges. Dissolved solids include salts, metals and minerals.

In some embodiments, the water source is contacted with a concentrated gemini surfactant composition at a temperature of about 50, 60, 70, 80, 90, 100, 110, 120, 130, 140, 150, 160, 170, 180, 190,200, 210, 220, 230, 240, or about 250° C., preferably around 60 to 200° C.

A gemini surfactant composition of the invention may be prepared in concentrated form or in a form more concentrated than that used during oil field operations such as fracking. A concentrate may contain 1, 2, 5, 10, 20, 30, 40, 50, 60, 70, 80, 95 to >95 wt % actives based on the weight of the concentrate, where actives represent a total of the combined gemini surfactants, monomer surfactants, and demulsifiers based on the weight of the concentrate. Some examples of a degree of concentration range from >1, 2, 5, 10, 20, 50 or 100× (or any intermediate value) the diluted strength of the composition as injected into a wellbore. A preferred range of concentration of a gemini surfactant in the injectate, is from to 0.5 wt %, preferably 0.2-0.4 wt % based on the total weight of the injectate fluid.

A concentrate containing one or more gemini surfactants of the invention may be storage stable, for example, ten days, two weeks, 1, 2, 3, 4, 5, 6 or >6 months under ambient temperatures such as between 0, 5, 10, 15, 20, 25, 30, 35 and 40° C. Aqueous solutions containing the gemini surfactants may be stable at 90° C. for a week, ten days, two weeks or more than two weeks and were also determined to be stable to temperatures up to 200° C.

Aqueous solutions of the gemini surfactants of the invention have higher storage life and thermal stability compared to other surfactants used in petroleum industry. For example, sodium dodecyl sulfate (SDS) undergoes hydrolysis at high temperature and prolonged heating at 40° C. or higher causes decomposition of SDS. Aqueous solutions of the gemini surfactants can be heated at 50° C., 75° C. or 100° C. under the same conditions without showing more than 5%, 4%, 1% or 0.5% decomposition of the gemini surfactants based on the total weight of the gemini surfactants before and after heating.

An injectate may be prepared from a concentrate or from its individual ingredients. For purposes of increasing hydrocarbon recovery an injectate may comprise <0.001, 0.001, 0.002, 0.005, 0.01, 0.01, 0.02, 0.05, 0.1, 0.2, 0.3, 0.4, 0.5, 0.6, 0.7, 0.8, 0.9, 1, 2, 3, 4, 5, 6, 7, 8, 9 10 or >10 wt % of a gemini surfactant (or any intermediate value within this range). In some embodiments an injectate comprises about 99, 99.9, 99.99 to 99.999 wt % of a water source and about 0.001, 0.01, 0.1 to 1 wt % of actives, such as one or more gemini surfactants or a mixture of gemini surfactant with other conventional actives.

Another embodiment of the invention is directed to a method for increasing a recovery of crude oil or other hydrocarbon from a subterranean hydrocarbon-containing formation, such as during hydraulic fracturing. This method includes those directed to recovering hydrocarbons from a subterranean hydrocarbon-containing formation that is a carbonate reservoir or otherwise contains carbonates, or a sandstone reservoir as well as from tight shale reservoirs formed by hydraulic fracturing or "fracking".

This method includes injecting or otherwise contacting a composition comprising the gemini surfactant as disclosed herein with a subterranean hydrocarbon-containing formation. The injected composition contains at least one gemini surfactant of the invention and optionally, a cationic monomer surfactant, a demulsifier, a water source, and/or a coupling agent, or a combination of two or more thereof. The method proceeds by injecting the composition into a hydrocarbon-containing subterranean fractured rock formation; and collecting a hydrocarbon from the hydrocarbon-containing subterranean fractured rock formation. Any water source may be used to produce the composition for injection including produced water or flowback water. As disclosed above, a composition for injection will contain an amount of one or more gemini surfactants of the invention sufficient to enhance the recovery of a hydrocarbon, for example, it may contain the at least one gemini surfactant at a concentration of <0.001, 0.001, 0.002, 0.005, 0.01, 0.02, 0.05, 0.1, 0.2, 0.5, 1, 2, 5, 10, 20 or >20 wt. This range includes all intermediate values and subranges. The preferred range of concentration is ranged from 0.1 to 0.5 wt % used as a single component in an injectate.

The method may be performed by injecting the composition into a first wellbore connected to the subterranean hydrocarbon-containing fractured rock formation and then recovering hydrocarbon from a second wellbore that is connected to the subterranean hydrocarbon-containing fractured rock formation; or by injecting the composition into a wellbore connected to the subterranean hydrocarbon-containing fractured rock formation, and then recovering the hydrocarbon from the same wellbore. In some embodiments, the composition will be produced from a concentrate containing the at least one gemini surfactant and other actives, such as monomeric surfactants and other ingredients described herein or known in the art for incorporation into an injectate or fracturing solution. Some examples of a degree of concentration range from >1, 2, 5, 10, 20, 50, 100, 200 or >200× (or any intermediate value) the diluted strength of the composition injected into a wellbore.

In some embodiments, a concentrate may be injected simultaneously with water, such as produced water into a wellbore in an amount sufficient to produce the desired dilution. In other embodiments, the composition for injection will be premixed with water to its final strength prior to injection.

In some embodiments, a concentrated or diluted gemini surfactant containing composition is first injected into a first wellbore connected to the subterranean hydrocarbon-containing formation, and the collecting is from a second wellbore that is connected to the subterranean hydrocarbon-containing formation. In other embodiments, the injecting and the collecting are carried out in the same wellbore.

Examples

Gemini surfactants according to the invention were synthesized and tested as described below.

Materials. Dodecanoic acid (98%, Sigma), oleic acid (92%, biochemical), 3-(dimethylamino)-1-propylamine (99%, GC, Aldrich), 1,4-dibromobutane (99%, Aldrich), trans-1,4-dibromo-2-butene (99%, Aldrich), cis-1,4-dichloro-2-butene (95%, Aldrich), 1,6-dibromohexane (96%, Aldrich), aluminum oxide (fluka) were utilized as obtained. Distilled solvents were used for the synthesis of the gemini surfactants.

Figure 11:
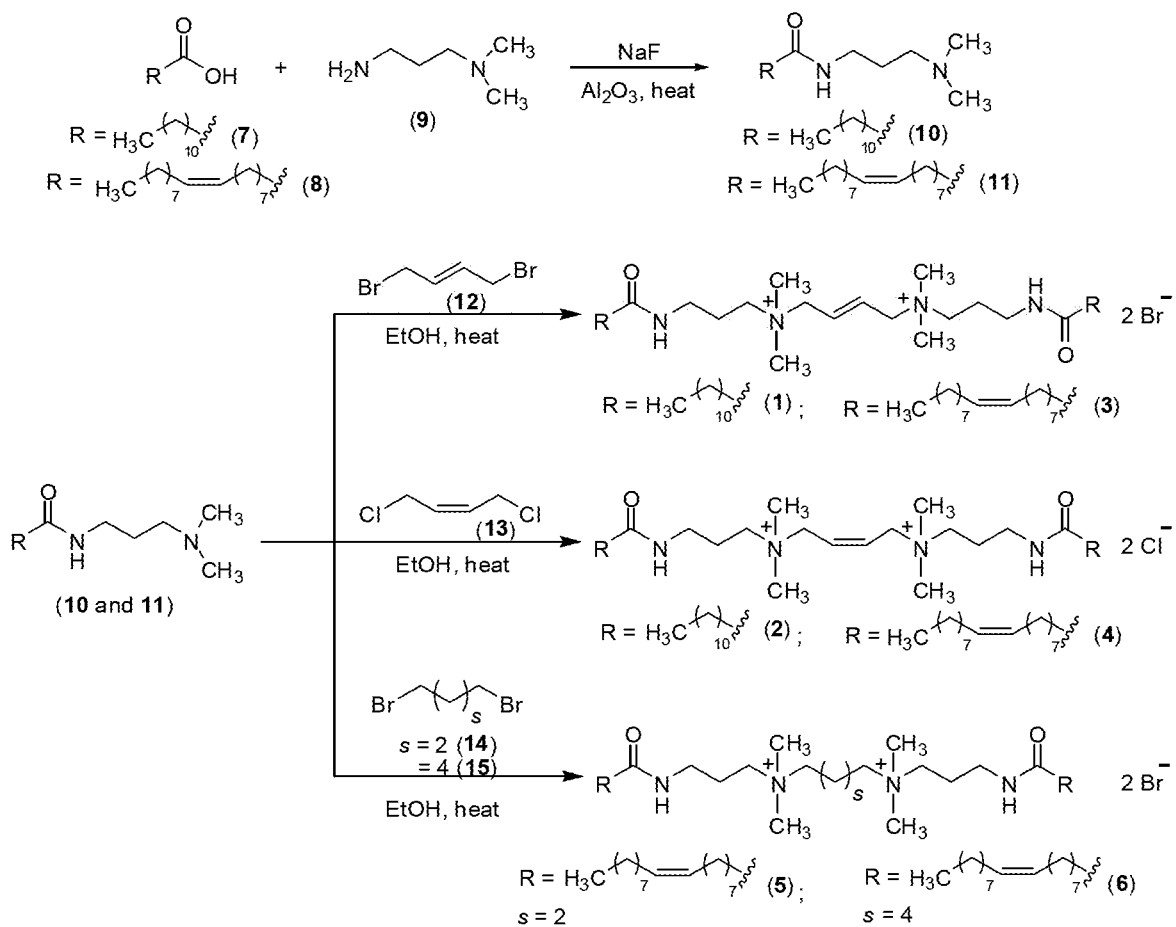
FIG. 11 depicts surfactant synthesis Scheme 1.

Synthesis and spectral characterization of amido-amine intermediate (10 and 11). The synthesis of amido-amine intermediate compound (10) was achieved using improved method described by Chu and co-workers as outlined in Scheme 1 which describes the synthesis of amido-amine-based cationic gemini surfactants (1)-(6) (FIG. 11); see Chu Z, Feng Y (2009) *A facile route towards the preparation of ultra-long-chain amidosulfobetaine surfactants.* Synlett (16):2655-2658, incorporated herein by reference in its entirety.

Dodecanoic acid (7) (20.00 g, 99.84 mmol), 3-(dimethylamino)-1-propylamine (9) (20.40 g, 200 mmol), and sodium fluoride (NaF) (0.42 g, 9.98 mmol) were added in a 100 mL flask connected with reflux condenser and the condenser was further connected with bent distilling adapter filled with $Al_2O_3$ in order to absorb the byproduct $H_2O$. The experiment was continued under reflux at 160° C. for six-hour in an argon atmosphere.

After six hours, further 3-(dimethylamino)-1-propylamine (15.30 g, 150 mmol) was introduced into the flask and the reaction was left to progress under the same experimental conditions for another five hours.

After completion, the unreacted 3-(dimethylamino)-1-propylamine was separated and the residue was washed three times with a mixture of cold water: acetone (7:93) then vacuumed to form intermediate (10); Ghumare A K, Pawar B V, Bhagwat S S (2013) *Synthesis and antibacterial activity of novel amido-amine-based cationic Gemini surfactants.* Journal of Surfactants and Detergents 16 (1):85-93, incorporated herein by reference in its entirety.

Intermediate (11) was prepared by adopting same method of intermediate (10). These procedures produced compounds (10) and (11) as described below.

N-dodecanamidopropyl-N,N-dimethylamine (10): White solid (25.90 g, 91% yield) $^1$H NMR (500 MHz, $CDCl_3$) δ (ppm): 0.83 (t, J=6.7 Hz, 3H), 1.15-1.25 (m, 16H), 1.51-1.58 (m, 2H), 1.64-1.73 (m, 2H), 2.11 (t, J=7.6 Hz, 2H), 2.30 (s, 6H), 2.47 (t, J=6.4 Hz, 2H), 3.29 (pent, J=5.8 Hz, 2H), 6.99 (s, 1H (NH). $^{13}$C NMR (125 MHz, $CDCl_3$) δ (ppm): 14.0, 22.6, 25.7, 29.2, 29.3, 29.4, 29.5, 31.8, 36.8, 38.5, 44.8, 58.0, 173.3.

N-oleamidopropyl-N,N-dimethylamine (11): Pale yellow viscous liquid (22.7 g, 87% yield). $^1$H NMR (500 MHz, $CDCl_3$) δ (ppm): 0.83 (t, J=6.7 Hz, 3H), 1.18-1.28 (m, 20H), 1.52-1.59 (m, 2H), 1.62-1.69 (m, 2H), 1.91-1.98 (m, 4H), 2.10 (t, J=7.6 Hz, 2H), 2.26 (s, 6H), 2.42 (t, J=6.4 Hz, 2H), 3.28 (pent, J=5.8 Hz, 2H), 5.25-5.31 (m, 2H), 7.0 (s, 1H (NH). $^{13}$C NMR (125 MHz, $CDCl_3$) δ (ppm): 14.0, 22.6, 25.7, 25.8, 27.1, 29.1, 29.2, 29.4, 29.6, 29.7, 31.8, 36.8, 38.7, 44.9, 58.0, 129.7, 129.9, 173.2.

Synthesis and spectral characterization of amido-amine cationic Gemini surfactants (1) and (2). The amido-amine intermediate compound (10) (10.0 g, 35.15 mmol) was treated with trans-1,4-dibromo-2-butene (12) (3.0 g, 14.06 mmol) in dry ethanol (5 mL) under reflux (80° C.) for 48 h (Scheme 1). After completion, the product was separated and recrystallized using solvent mixture acetone/ethyl acetate to form the required gemini surfactant 1 as a white solid; Zana R et al. (1991).

Gemini surfactant (2) was synthesized by adopting the same procedure of (1). Resulting surfactants (1) and (2) are described below.

(E)-dodecanoic acid [3-({4-[(3-dodecanoylamino-propyl)-dimethyl-amino]but-2-enyl}-dimethyl-amino)-propyl]-amide dibromide (1): White solid (9.70 g, 88% yield based on trans-1,4-dibromo-2-butene). $^1$H NMR (500 MHz, $CDCl_3$) δ (ppm): 0.82 (t, J=6.7 Hz, 6H), 1.16-1.26 (m, 32H), 1.52-1.58 (m, 4H), 2.06-2.12 (m, 4H), 2.26-2.33 (m, 4H), 3.31 (s, 12H), 3.32-3.36 (m, 4H), 3.64-3.72 (m, 4H), 4.41-4.49 (m, 4H), 6.77-6.85 (m, 2H), 8.16 (s, 2H (NH). $^{13}$C NMR (125 MHz, $CDCl_3$) δ (ppm): 14.0, 22.6, 22.8, 25.9, 29.3, 29.4, 29.5, 29.6, 29.7, 31.8, 36.1, 36.6, 51.0, 62.6, 65.0, 130.2, 175.3. FTIR (KBr pellet) υ ($cm^{-1}$) 3441 ($υ_{N-H}$, secondary amine), 2922 and 2850 ($υ_{C-H}$, aliphatic asymmetric and symmetric respectively), 1641 (amide I band), 1555 (amide II band). Anal. Calcd for $C_{38}H_{78}O_2N_4Br_2$ (782.86): C, 58.30; H, 10.04; N, 7.16. Found: C, 58.17; H, 10.19; N, 7.08.

(Z)-dodecanoic acid [3-({4-[(3-dodecanoylamino-propyl)-dimethyl-amino]but-2-enyl}-dimethyl-amino)-propyl]-amide dichloride (2): White solid (11.85 g, 71% yield based on cis-1,4-dichloro-2-butene). $^1$H NMR (500 MHz, $CDCl_3$) δ (ppm): 0.83 (t, J=6.7 Hz, 6H), 1.18-1.28 (m, 32H), 1.55-1.61 (m, 4H), 2.06-2.12 (m, 4H), 2.28-2.34 (m, 4H), 3.29 (s, 12H), 3.30-3.36 (m, 4H), 3.63-3.71 (m, 4H), 4.67-4.73 (m, 4H), 6.38-6.44 (m, 2H), 8.52 (s, 2H (NH). $^{13}$C NMR (125 MHz, $CDCl_3$) 3 (ppm): 14.1, 22.7, 22.9, 26.0, 29.3, 29.4, 29.5, 29.6, 29.7, 31.9, 35.9, 36.6, 50.5, 60.8, 62.3, 128.1, 175.5. FTIR (KBr pellet) υ ($cm^{-1}$) 3475 ($υ_{N-H}$, secondary amine), 2924 and 2852 ($σ_{C-H}$, aliphatic asymmetric and symmetric respectively), 1642 (amide I band), 1545 (amide II band). Anal. Calcd for $C_{38}H_{78}O_2N_4Cl_2$ (693.96): C, 65.77; H, 11.33; N, 8.07. Found: C, 65.65; H, 11.41; N, 8.02.

Synthesis and spectral characterization of amido-amine cationic Gemini surfactants (3)-(6). The amido-amine intermediate compound (11) (10.0 g, ×27.28 mmol) was treated with trans-1,4-dibromo-2-butene (12) (2.33 g, 10.91 mmol) in dry ethanol (5 mL) for 48 h under reflux (80° C.). After completion, the reaction product was purified using silica gel column chromatography with methanol:acetone (3:7) as eluent to afford required gemini surfactant (3); Zana R et al. (1991).

Gemini surfactants (4)-(6) of this series were synthesized by adopting the same procedure of (3). The resulting surfactants are described below.

(E)-oleic acid [3-({4-[(3-oleamidopropyl)-dimethylamino]but-2-enyl}-dimethyl-amino)-propyl]-amide dibromide (3): Pale yellow viscous oil (8.49 g, 82% yield based on trans-1,4-dibromo-2-butene). $^1$H NMR (500 MHz, CDCl$_3$) δ (ppm): 0.82 (t, J=6.7 Hz, 6H), 1.18-1.28 (m, 40H), 1.49-1.55 (m, 4H), 1.91-1.97 (m, 8H), 2.0-2.06 (m, 4H), 2.21 (t, J=7.6 Hz, 4H), 3.23 (s, 12H), 3.24-3.30 (m, 4H), 3.52-3.58 (m, 4H), 4.27-4.33 (m, 4H), 5.23-5.33 (m, 4H), 6.62-6.68 (m, 2H), 7.79 (s, 2H (NH)). $^{13}$C NMR (125 MHz, CDCl$_3$) δ (ppm): 14.0, 22.6, 23.0, 25.7, 27.2, 29.3, 29.4, 29.5, 29.7, 29.8, 31.8, 36.4, 51.1, 62.6, 64.9, 129.5, 129.9, 130.2, 174.8. FTIR (KBr pellet) υ (cm$^{-1}$) 3445 ($υ_{N-H}$, secondary amine), 2926 and 28547 ($υ_{C-H}$, aliphatic asymmetric and symmetric respectively), 1643 (amide I band), 1551 (amide II band). Anal. Calcd for C$_{50}$H$_{98}$O$_2$N$_4$Br$_2$ (947.15): C, 63.40; H, 10.43; N, 5.92. Found: C, 63.32; H, 10.57; N, 5.82.

(Z)-oleic acid [3-({4-[(3-oleamidopropyl)-dimethylamino]but-2-enyl}-dimethyl-amino)-propyl]-amide dichloride (4): Pale yellow viscous oil (12.80 g, 80% yield based on cis-1,4-dichloro-2-butene). $^1$H NMR (500 MHz, CDCl$_3$) δ (ppm): 0.83 (t, J=6.7 Hz, 6H), 1.17-1.27 (m, 40H), 1.47-1.55 (m, 4H), 1.91-1.97 (m, 8H), 1.99-2.05 (m, 4H), 2.20 (t, J=7.6 Hz, 4H), 3.23 (s, 12H), 3.24-3.30 (m, 4H), 3.53-3.59 (m, 4H), 4.52-4.58 (m, 4H), 5.22-5.32 (m, 4H), 6.32-6.38 (m, 2H), 8.0 (s, 2H (NH)). $^{13}$C NMR (125 MHz, CDCl$_3$) δ (ppm): 14.0, 22.6, 23.0, 25.9, 27.2, 29.3, 29.4, 29.5, 29.7, 29.8, 31.8, 36.3, 50.6, 60.6, 62.3, 127.7, 129.5, 129.9, 174.8. FTIR (KBr pellet) υ (cm$^{-1}$) 3431 ($υ_{N-H}$, secondary amine), 2924 and 2853 ($υ_{C-H}$, aliphatic asymmetric and symmetric respectively), 1642 (amide I band), 1552 (amide II band). Anal. Calcd for C$_{50}$H$_{98}$O$_2$N$_4$Cl$_2$ (858.24): C, 69.97; H, 11.51; N, 6.53. Found: C, 69.84; H, 11.57; N, 6.63.

Oleic acid [3-({4-[(3-oleamidopropyl)-dimethyl-amino]butyl}-dimethyl-amino)-propyl]-amide dibromide (5): Pale yellow gel (9.3 g, 91% yield based on 1,4-dibromobutane). $^1$H NMR (500 MHz, CDCl$_3$) δ (ppm): 0.83 (t, J=6.7 Hz, 6H), 1.18-1.28 (m, 40H), 1.50-1.56 (m, 4H), 1.91-1.97 (m, 12H), 1.99-2.05 (m, 4H), 2.21 (t, J=7.6 Hz, 4H), 3.19 (s, 12H), 3.25-3.31 (m, 4H), 3.44-3.50 (m, 4H), 3.54-3.60 (m, 4H), 5.23-5.33 (m, 4H), 7.81 (s, 2H (NH)). $^{13}$C NMR (125 MHz, CDCl$_3$) δ (ppm): 14.1, 19.6, 22.6, 22.9, 25.9, 27.2, 29.3, 29.4, 29.5, 29.7, 29.8, 31.8, 36.4, 51.4, 62.3, 63.2, 129.6, 129.9, 174.9. FTIR (KBr pellet) υ (cm$^{-1}$) 3439 ($υ_{N-H}$, secondary amine), 2923 and 2851 ($υ_{C-H}$, aliphatic asymmetric and symmetric respectively), 1632 (amide I band), 1548 (amide II band). Anal. Calcd for C$_{50}$H$_{100}$O$_2$N$_4$Br$_2$ (949.16): C, 63.27; H, 10.62; N, 5.90. Found: C, 63.21; H, 10.57; N, 5.87.

Oleic acid [3-({6-[(3-oleamidopropyl)-dimethyl-amino]hexyl}-dimethyl-amino)-propyl]-amide dibromide (6): White solid (8.7 g, 93% yield based on 1,6-dibromohexane). $^1$H NMR (500 MHz, CDCl$_3$) δ (ppm): 0.82 (t, J=6.7 Hz, 6H), 1.17-1.27 (m, 40H), 1.46-1.52 (m, 4H), 1.54-1.60 (m, 4H), 1.91-1.97 (m, 12H), 2.02-2.08 (m, 4H), 2.33 (t, J=7.6 Hz, 4H), 3.26 (s, 12H), 3.33-3.39 (m, 4H), 3.53-3.59 (m, 4H), 3.69-3.75 (m, 4H), 5.23-5.33 (m, 4H), 8.40 (s, 2H (NH)). $^{13}$C NMR (125 MHz, CDCl$_3$) δ (ppm): 14.1, 21.6, 22.6, 22.7, 24.6, 25.9, 27.1, 29.1, 29.2, 29.3, 29.4, 29.6, 29.7, 31.8, 35.8, 51.1, 62.3, 65.0, 129.6, 129.9, 175.3. FTIR (KBr pellet) υ (cm$^{-1}$) 3440 ($υ_{N-H}$, secondary amine), 2924 and 2852 ($υ_{C-H}$, aliphatic asymmetric and symmetric respectively), 1633 (amide I band), 1549 (amide II band). Anal. Calcd for C$_{52}$H$_{104}$O$_2$N$_4$Br$_2$ (977.22): C, 63.91; H, 10.73; N, 5.73. Found: C, 63.78; H, 10.80; N, 5.64.

Analytical Equipment. The structures of the amido-amine-based cationic gemini surfactants (1)-(6) were established by using NMR, FTIR, and elemental analysis. The NMR data was acquired on 500 MHz NMR instrument (Jeol 1500 model). Deuterated chloroform was used as a solvent, TMS as an internal standard, and chemical shifts in NMR spectra were recorded in ppm. The FTIR (fourier transform infrared) spectroscopy was done using FTIR spectrophotometer (Perkin-Elmer 16F model) and spectra were recorded in wave numbers (cm$^{-1}$). Elemental analysis was obtained using Perkin Elmer Series 11 (CHNS/O) Analyzer 2400.

Thermogravimetric Analysis. Thermogravimetric analysis (TGA) was conducted using SDT Q600 apparatus from TA instruments with a constant heating rate of 20° C./min and the temperature range was 30-500° C. The experiment was run using an aluminum sample pan with nitrogen flow rate of 100 mL/min.

Long-Term Thermal Stability. Long-term thermal stability was assessed using a novel approach based on an aging technique. Aqueous solutions of gemini surfactants (1)-(6) were aged in a sealed tube for 10 days at 90° C. NMR ($^1$H, $^{13}$C) and FTIR instruments were used to identify the changes in the structure of the surfactants after aging.

Surface Properties. Surface tensions were identified with the help of pendant drop method at 20° C. using Biolin Scientific Attension instrument. Water was used as a solvent for all surface tension experiments. The reported data points of all surface tension measurements are average equilibrium values. The critical micelle concentration (cmc) was measured from the intersection point of two lines in the plot of surface tension versus concentration.

The synthesis of amido-amine-based cationic gemini surfactants (1)-(6) was achieved using an improved method outlined in scheme 1. The condensation of commercially available carboxylic acid (7) and (8) with 3-(dimethylamino)-1-propylamine (9) generated the amide intermediates (10) and (11). The reaction was followed by quaternization reaction with halohydrocarbons (12-15) yielding the desired amido-amine cationic gemini surfactants (1)-(6) with high yield; Ghumare A K (2013); and Zana R, Benrraou M, Rueff R (1991) *Alkanediyl-. alpha.,. omega.-bis (dimethylalkylammonium bromide) surfactants. 1. Effect of the spacer chain length on the critical micelle concentration and micelle ionization degree*. Langmuir 7 (6):1072-1075, each incorporated herein by reference in their entirety.

Structures of gemini surfactants and corresponding intermediates were confirmed by characterization techniques such as NMR, FTIR, and elemental analysis.

The six amido-amine-based cationic gemini surfactants exhibited nearly same peak pattern, therefore, the spectral characterization of gemini surfactant (1) and its intermediate (10) were highlighted as examples.

According to $^1$H NMR spectra of the intermediate compound (10), the terminal methyl protons [—(CH$_2$)$_n$—CH$_3$] resonated at δ=0.83 ppm and the methylene protons

[—(CH$_2$)$_n$—CH$_3$)] in the hydrophobic tail resonated at δ=1.15-1.25 ppm. The disappearance of hydroxyl proton in the carboxylic acid (—CH$_2$—C=O—OH) (8) at δ=10.25 ppm and the appearance of the amide proton (—CH$_2$—C=O—NH) (10) at δ=6.99 ppm were observed. The appearance of the methyl proton directly attached to the tertiary nitrogen [—CH$_2$—N—(CH$_3$)$_2$] at δ=2.30 confirmed the formation of intermediate compound (10).

According to $^{13}$C NMR spectra of intermediate compound (10), the terminal methyl carbon [—(CH$_2$)$_n$—CH$_3$)] resonated at δ=14.0 ppm and the methylene carbons [—(CH$_2$)$_n$—CH$_3$)] in the hydrophobic tail resonated at δ=22.6-36.8 ppm. The two methyl carbon directly attached to the tertiary nitrogen [—CH$_2$—N—(CH$_3$)$_2$] resonated at δ=44.8 ppm. The methylene carbon next to tertiary nitrogen [—CH$_2$—CH$_2$—N—(CH$_3$)$_2$] in compound (10) resonated at δ=58.0 ppm. The appearance of the carbonyl carbon of fatty acid (7) (—CH$_2$—C=O—OH) resonated at δ=180.4 ppm and then clear up field shift of the same carbonyl carbon in amide (10) (—CH$_2$—C=O—NH—) at δ=173.3 ppm confirmed the formation of intermediate (10).

According to $^1$H NMR spectra of gemini surfactant (1), the terminal methyl protons [—(CH$_2$)$_n$—CH$_3$)] resonated at δ=0.82 ppm and the methylene protons [—(CH$_2$)$_n$—CH$_3$)] in the hydrophobic tail resonated at δ=1.16-1.26 ppm. The methyl protons directly attached to the nitrogen [—CH$_2$—N—(CH$_3$)$_2$] that previously appeared at δ=2.30 ppm in intermediate (10) has shifted downfield to δ=3.31 ppm in the gemini surfactant (1) [—CH$_2$—N—(CH$_3$)$_2$—CH$_2$—]. The downfield shift of the amide proton (—CH$_2$—C=O—NH) from δ=6.99 ppm in compound 10 to δ=8.16 ppm in gemini surfactant 1 has been also detected. The olefinic protons in the spacer group [—N—CH$_2$—CH=CH—CH$_2$—N—] appeared at δ=6.77-6.85 ppm which further confirmed the formation of the gemini surfactant 1.

According to $^{13}$C NMR spectra of the gemini surfactant (1), the terminal methyl carbon [—(CH$_2$)$_n$—CH$_3$)] resonated at δ=14.0 ppm and the methylene carbons [—(CH$_2$)$_n$—CH$_3$)] in the hydrophobic tail resonated at δ=22.6-36.6 ppm. The two methyl carbons of the tertiary nitrogen [—CH$_2$—N—(CH$_3$)$_2$] that were resonated at δ=44.8 ppm in the intermediate (10) have shifted downfield to δ=51.0 ppm as evidence of the formation of the gemini surfactant 1. The two new peaks that appeared at δ=62.6 ppm and 65.0 ppm correspond to 2 methylene groups connected with nitrogen [—CH$_2$—N—(CH$_3$)$_2$—CH$_2$—]. The olefinic carbon in spacer group [—N—CH$_2$—CH=CH—CH$_2$—N-] resonated at δ=130.2 ppm. The carbonyl carbon (—CH$_2$—C=O—NH—) peak was detected at δ=175.3 ppm.

In general, the NMR ($^1$H and $^{13}$C) spectral data appeared to be compatible with the proposed structures of the gemini surfactant 1.

In FTIR spectra of the gemini surfactant 1, a disappearance of the hydroxyl group of fatty acid (7) (—CH$_2$—C=O—OH) ranged from 2400 to 3400 cm$^{-1}$ and an existence of amide (—CH$_2$—C=O—NH) at 3441 cm$^{-1}$ as well as a shifting of the band of carbonyl stretching (—C=O—) from the region of acid (—CH$_2$—C=O—OH) at 1710 cm$^{-1}$ to the region of amide (—CH$_2$—C=O—NH—) at 1641 cm$^{-1}$ were observed. Amide I band resonated at 1641 cm$^{-1}$ and amide II band resonated at 1555 cm$^{-1}$; Ghumare A K (2013). The two stretching vibrations at 2922 cm$^{-1}$ (CH aliphatic symmetric) and 2850 cm$^{-1}$ (CH aliphatic asymmetric) were also detected which confirmed the formation of the gemini surfactant (1); Dardir M, Mohamed D, Farag A, Ramdan A, Fayad M (2016) *Preparation and evaluation of cationic bolaform surfactants for water-based drilling fluids*. Egyptian Journal of Petroleum; Shaban S M, Aiad I, Fetouh H A, Maher A (2015) *Amidoamine double tailed cationic surfactant based on dimethylaminopropylamine: Synthesis, characterization and evaluation as biocide*. Journal of Molecular Liquids 212:699-707; and El-Lateef H M A, Abo-Riya M A, Tantawy A H (2016), *Empirical and quantum chemical studies on the corrosion inhibition performance of some novel synthesized cationic Gemini surfactants on carbon steel pipelines in acid pickling processes*. Corrosion Science 108:94-110, each incorporated herein by reference in their entirety.

Thermal Stability of Gemini Surfactants (1)-(6). Thermal stability is an essential property of surfactants for various oilfield applications. A surfactant, which designed to be used in surfactant flooding, should be thermally stable at high reservoir temperature (≥90° C.) because it may stay inside oil reservoir for many days. The high temperature in a reservoir can cause surfactant precipitation due to thermal degradation and the surfactant ability to reduce interfacial tension between water and oil can be decreased significantly.

The short-term and long-term thermal stability of the synthesized gemini surfactants (1)-(6) were investigated. The short-term stability was assessed with the help of TGA instrument and the graph exhibited excellent thermal stability of the gemini surfactants (1-6) with no thermal degradation up to 200° C. (FIG. 2). The long-term thermal stability of the gemini surfactants (1)-(6) was examined using a novel approach based on aging technique where the aqueous solutions of surfactants were aged in a sealed tube at 90° C. for 10 days. NMR ($^1$H, $^{13}$C) and FTIR instruments were used to study the change in the structure of the surfactants after aging at a different period. However, only FTIR and NMR spectra of the 10 days aged surfactants were presented. The six amido-amine cationic gemini surfactants (1)-6) exhibited excellent long-term thermal stability with no thermal degradation after 10 days aging. Spectral characterization of the 10 days aged sample of gemini surfactant (1) and (6) were highlighted as examples.

Figure 3:
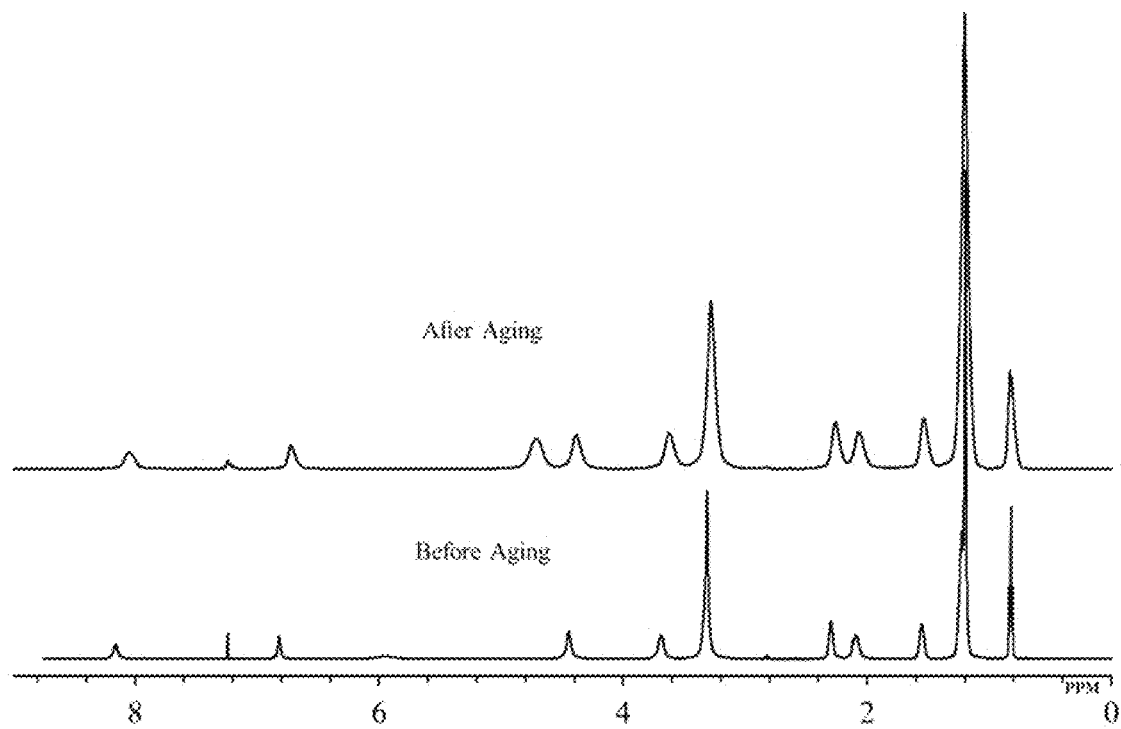
FIG. 3. $^1$H NMR spectra of the gemini surfactant (1) before and after aging.
Figure 5:
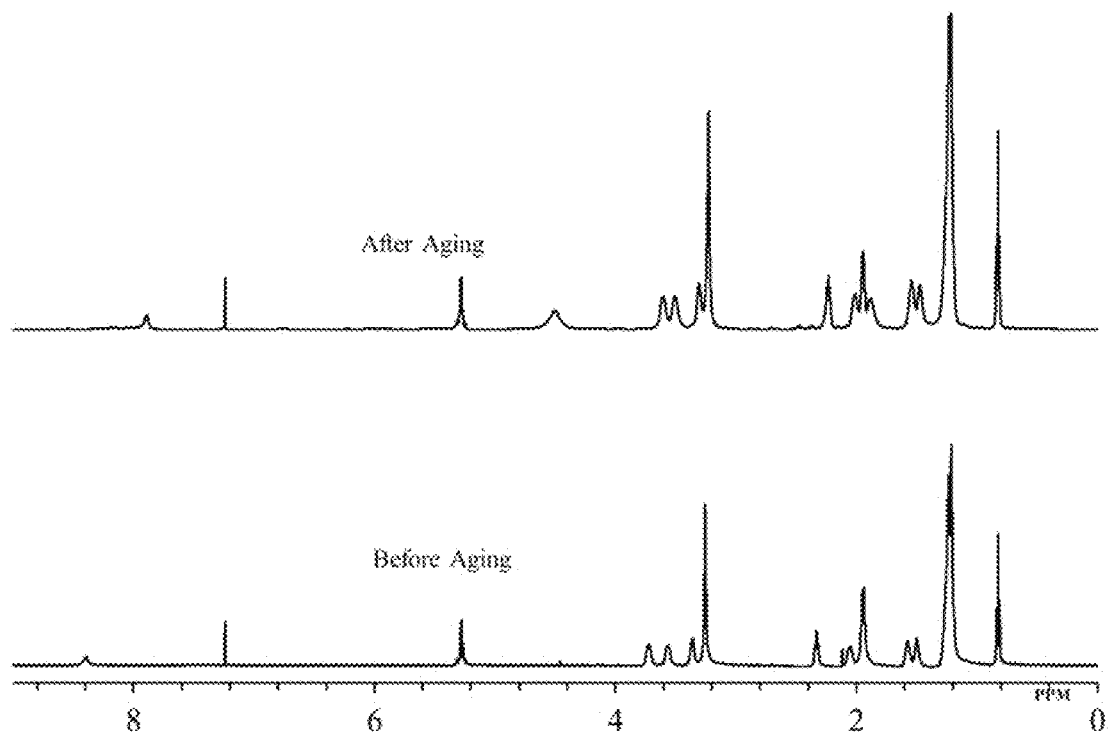
FIG. 5. $^1$H NMR spectra of the gemini surfactant (6) before and after aging.

The $^1$H NMR spectra of the 10 days aged samples of the gemini surfactants (1) and (6) (FIGS. 3 and 5) demonstrated the appearance of the protons of the terminal methyl group [—(CH$_2$)$_n$—CH$_3$)] as well as protons of the methylene group [—(CH$_2$)$_n$—CH$_3$)] of the surfactant hydrophobic tail. The olefinic protons in the hydrophobic tail of the gemini surfactants 6 (FIG. 5) were also revealed. Similarly, the olefinic protons in the spacer group of 10 days aged sample of gemini surfactants 1 (FIG. 3) were also detected. Likewise, the methylene protons in the spacer group of gemini surfactants 6 (FIG. 5) equally appeared. The protons of methyl group directly attached with quaternary nitrogen [—CH$_2$—N$^+$—(CH$_3$)$_2$—CH$_2$-] clearly observed. In addition, the appearance of the amide proton (—CH$_2$—C=O—NH—) confirmed the survival of Gemini surfactants (1) and (6) in harsh conditions. An additional peak at δ=4-5 ppm appeared in after aging sample correspond to residual water; Fulmer G R, Miller A J, Sherden N H, Gottlieb H E, Nudelman A, Stoltz B M, Bercaw J E, Goldberg K I (2010) *NMR chemical shifts of trace impurities: common laboratory solvents, organics, and gases in deuterated solvents relevant to the organometallic chemist*. Organometallics 29 (9):2176-2179, incorporated herein by reference in its entirety.

According to $^{13}$C NMR spectra of the 10 days aged samples of gemini surfactants (1) and (6)(FIGS. 4 and 6), the methyl [—(CH$_2$)$_n$—CH$_3$)] and methylene carbon in hydrophobic tail of gemini surfactants (1) and (6) were clearly identified. The two methyl carbon [—CH$_2$—N$^+$—(CH$_3$)$_2$—

Figure 4:
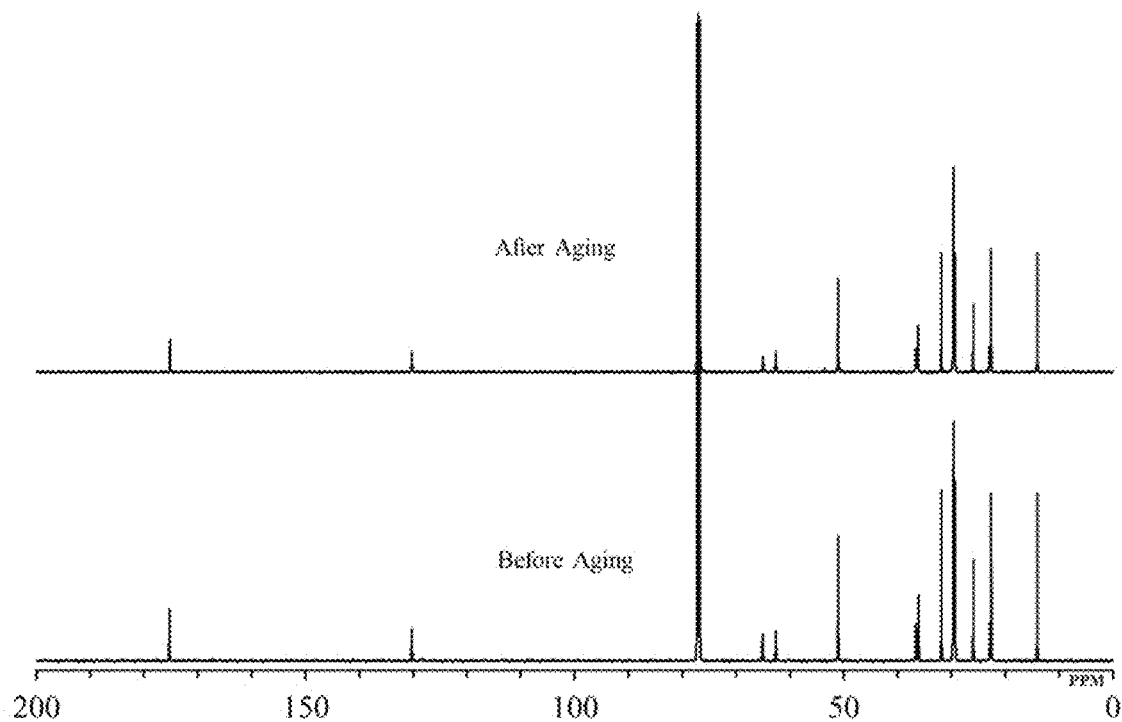
FIG. 4. $^{13}$C NMR spectra of the gemini surfactant (1) before and after aging.
Figure 6:
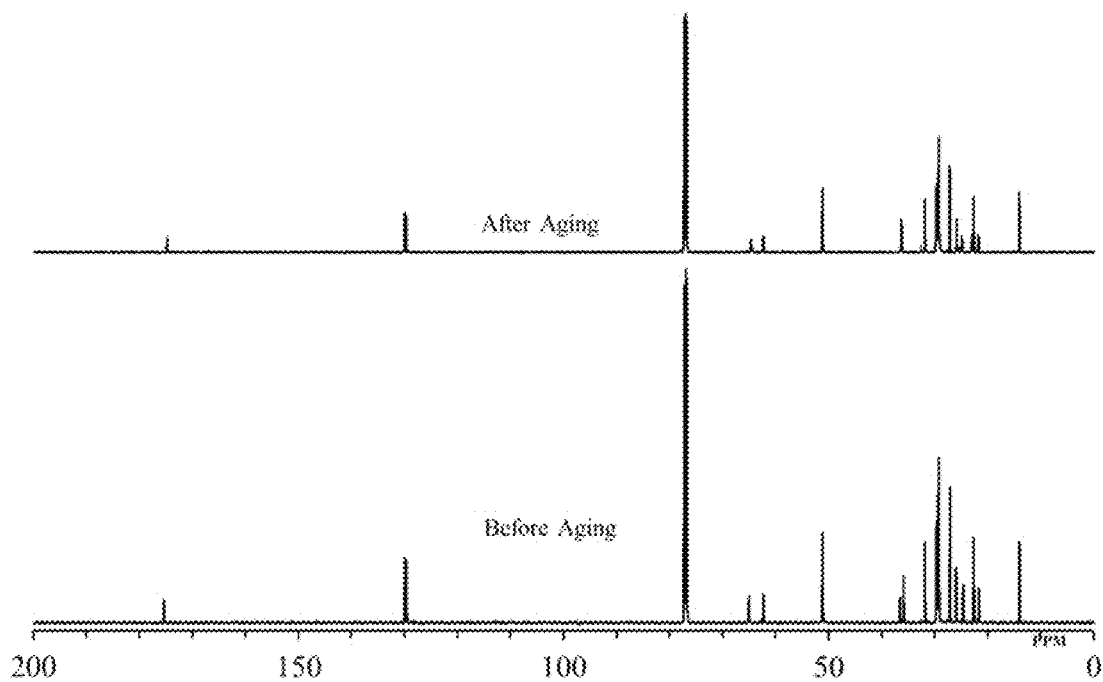
FIG. 6. $^{13}$C NMR spectra of the gemini surfactant (6) before and after aging.

CH$_2$-] and two methylene carbon [—CH$_2$—N$^+$(CH$_3$)$_2$—CH$_2$-] directly attached to the quaternary nitrogen were similarly observed in both surfactants (1) and (6) (FIGS. 4 and 6). The olefinic carbon in hydrophobic tail of gemini surfactant (6) (FIG. 6) as well as the olefinic carbon in spacer group of gemini surfactant 1 (FIG. 4) were also detected. The carbonyl carbon of amide group [—CH$_2$—C=O—NH] was clearly shown in both surfactants.

Figure 7:
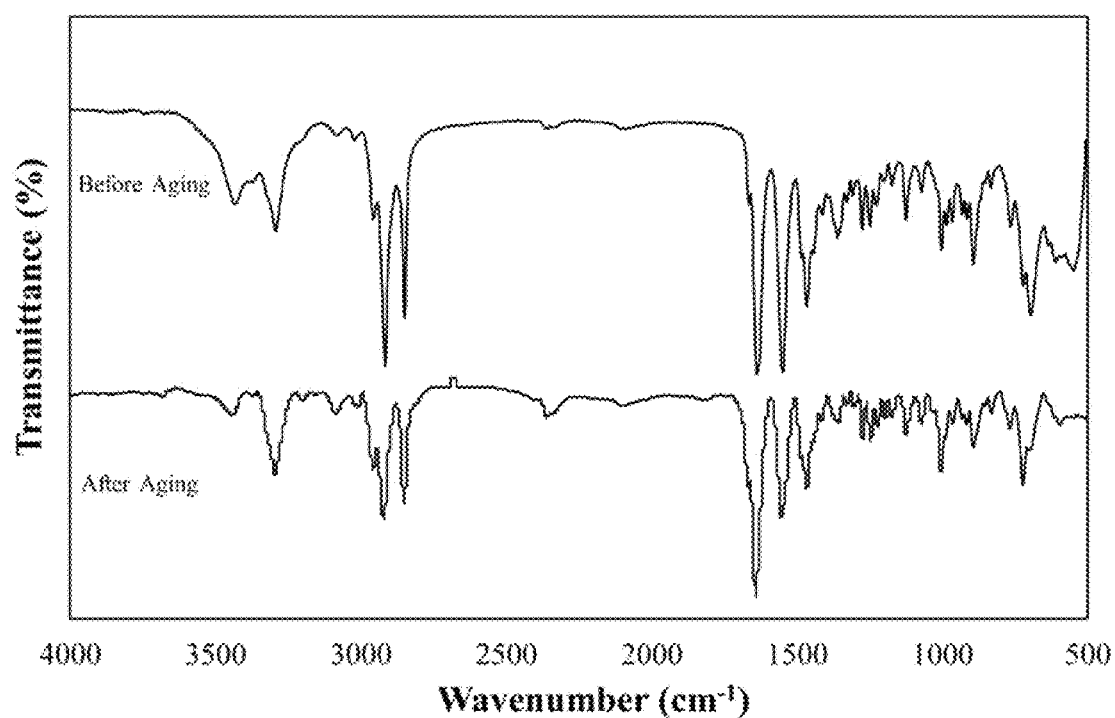
FIG. 7. FTIR spectra of the gemini surfactant (1) before and after aging.
Figure 8:
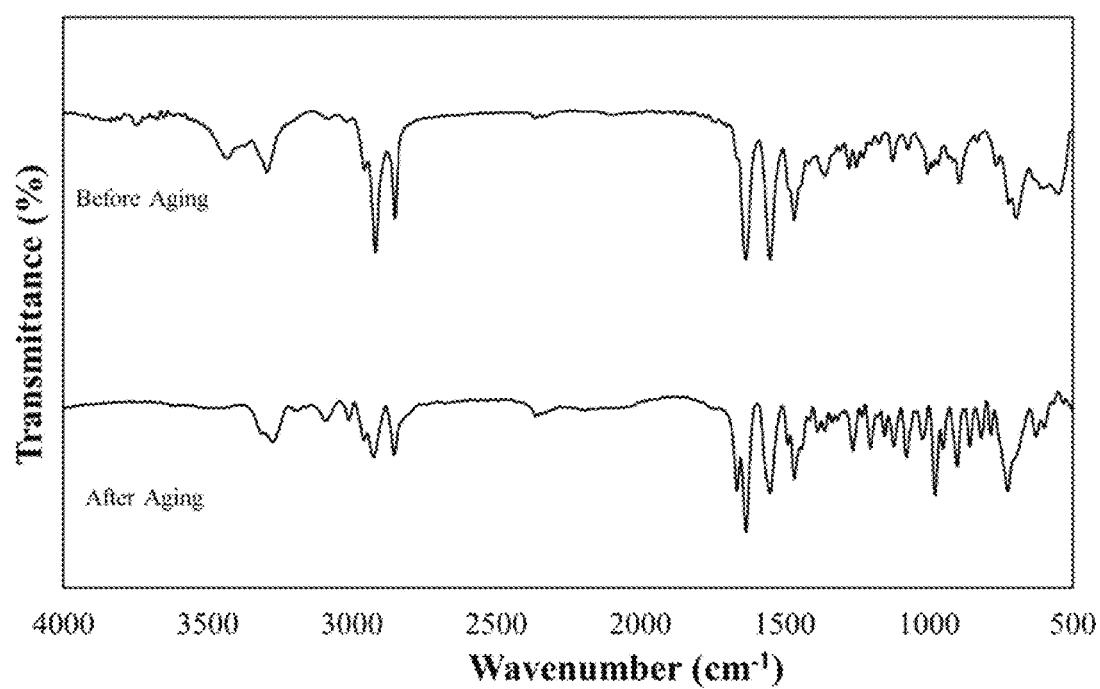
FIG. 8. FTIR spectra of the gemini surfactant (6) before and after aging.

In general, the NMR ($^1$H and $^{13}$C) spectra of the aged samples of gemini surfactants (1 and 6) confirmed that no structural changes occurred. According to the FTIR spectra of 10 days aged samples of gemini surfactants (1) and (6) (FIGS. 7 and 8), the two clear stretching bands in the region of 2921 cm$^{-1}$ and 2850 cm$^{-1}$ were detected and they correspond to CH aliphatic symmetric and CH aliphatic asymmetric respectively. The carbonyl stretching and C—N stretching were also observed which confirmed the structure of gemini surfactants (1) and (6) and showed the thermal stability of amido-amine cationic gemini surfactants. There was no cloudiness and phase separation before and after aging at 90° C.; therefore, the cloud points of the surfactants were >90° C.

Figure 9:
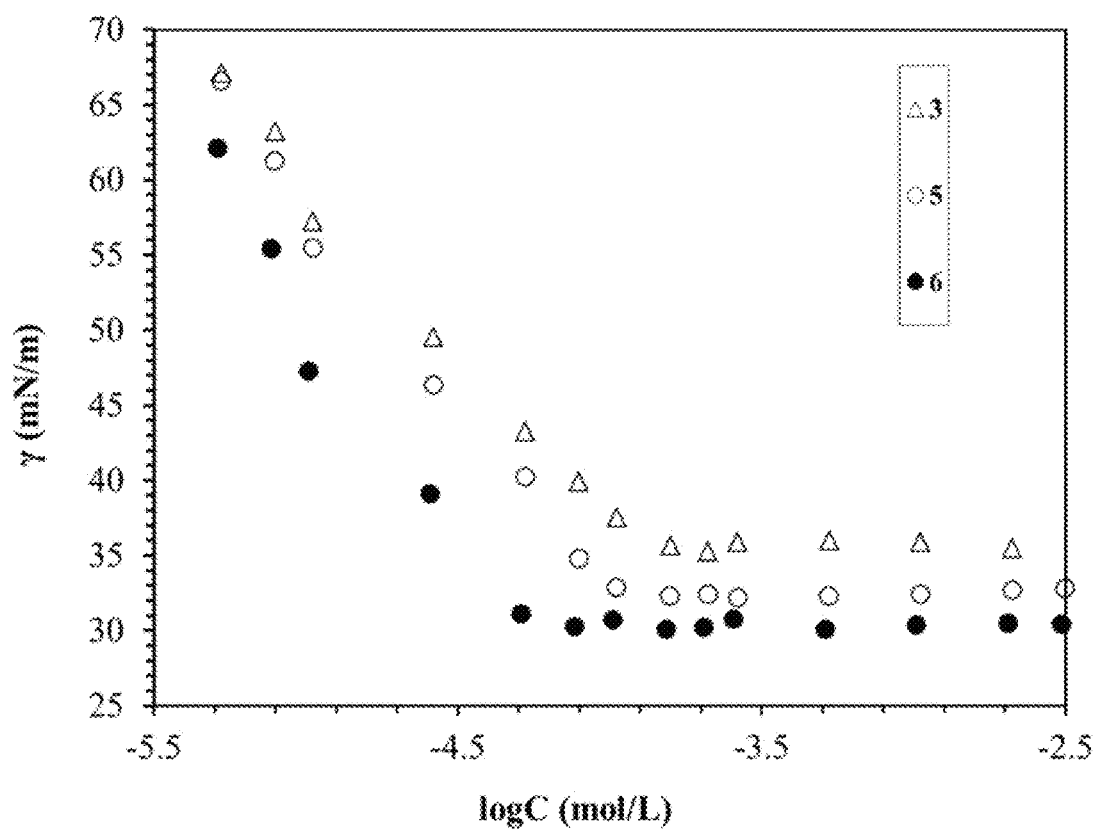
FIG. 9. Effect of spacer length and spacer rigidity on the surface tension.
Figure 10:
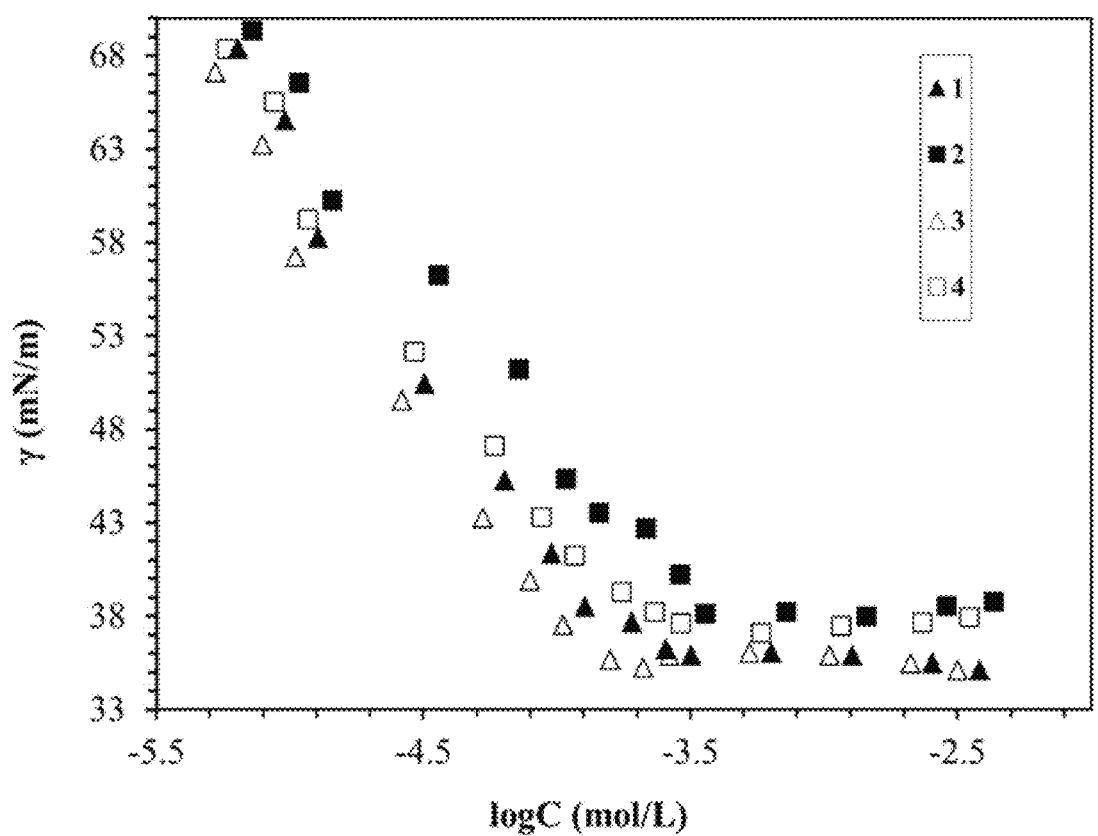
FIG. 10. Effect of chain length and spacer orientation on the surface tension.

Surface Tension Measurements. The synthesized gemini surfactants (1)-(6) showed good water solubility and surface tension was identified at 25° C. FIGS. 9 and 10 exhibited surface tension of all surfactants at different concentrations, while other surface properties are given in Table 1. The surface tension remarkably decreased upon addition of more surfactant up to the breakpoint at cmc. Further addition of surfactant above cmc showed no change in the surface tension. The surfactant 2 showed the highest surface tension while the surfactant 6 showed the least surface tension at all investigated concentrations. The surface properties can be related to the different chain length, spacer length, spacer rigidity, and to the presence of different counterions in the gemini surfactants.

TABLE 1

Surface properties of Gemini surfactants (1)-(6)

| Surfactants | cmc (mol L$^{-1}$) | $\gamma_{cmc}$ (mN m$^{-1}$) | $\pi_{cmc}$ (mN m$^{-1}$) | $\Gamma_{max} \times 10^6$ (mol m$^{-2}$) | $A_{min}$ (nm$^2$) |
|---|---|---|---|---|---|
| 1 | 2.56 × 10$^{-4}$ | 36.23 | 35.77 | 1.81 | 0.91 |
| 2 | 3 61 × 10$^{-4}$ | 38.12 | 33.88 | 1.60 | 1.05 |
| 3 | 1.58 × 10$^{-4}$ | 35.67 | 36.33 | 1.92 | 0.86 |
| 4 | 2.91 × 10$^{-4}$ | 37.23 | 34.77 | 1.64 | 1.01 |
| 5 | 1.05 × 10$^{-4}$ | 32.92 | 39.08 | 2.26 | 0.73 |
| 6 | 0.77 × 10$^{-4}$ | 30.34 | 41.66 | 2.38 | 0.70 |

FIG. 9 shows the effect of the spacer length and rigidity on the surface tension of the gemini surfactants. By comparing the surfactant (5) and (6), it was observed that the surfactant with a larger spacer (6) showed lower cmc which could be associated to the hydrophobic nature of longer spacer; Chavda S, Bahadur P Aswal V K (2011) *Interaction between nonionic and Gemini (cationic) surfactants: effect of spacer chain length*. Journal of Surfactants and Detergents 14 (3):353-362, incorporated herein by reference in its entirety.

The rigidity of spacer is another important parameter in determining the aggregation morphologies of the gemini surfactants. Surfactant (3) and surfactant (5) possess almost similar structures but the spacer of surfactant (3) is more rigid compared to the surfactant (5). The gemini surfactant (3) with more rigid spacer demonstrated a higher cmc and corresponding surface tension at cmc ($\gamma_{cmc}$). The cmc and $\gamma_{cmc}$ of gemini surfactant (3) were 1.58×10$^{-4}$ mol L$^{-1}$ and 35.67 mN m$^{-1}$, respectively, which is much higher as compared to the surfactant 5 that has a relatively flexible spacer. The gemini surfactants containing rigid spacer usually make vesicles. On the other hand, the gemini surfactants without rigidity can form a mixture of vesicles and micelles; Zhu D-Y et al. (2012).

Chain length of a surfactant is another critical parameter that affects the surface properties of surfactant. FIG. 10 compares the surface tension of the gemini surfactants with different chain length and spacer orientation. By comparing the surfactants (1) and (3), the cmc and the corresponding $\gamma_{cmc}$ were decreased when the hydrophobic tail was increased from 12 carbons (1) to 18 carbons (3). A similar trend was observed with the surfactants (2) and (4), which also have the same spacer and counterions but differ with each other by the length of the hydrophobic tail.

The double bond in spacer of the surfactant (1) and (3) was in trans conformation with bromide counterions while the double bond in spacer of surfactant (2) and (4) was in cis conformation with chloride counterions. The cmc and the $\gamma_{cmc}$ of the surfactant 2 and 4 were higher as compared to the analogous surfactant (1) and (3) respectively. The difference of surface properties between the surfactants (1), (2) and (3), (4) may be associated with the different conformation of spacer double bond and counters ions. It has been reported previously that the presence of different counterions in the spacer can alter the cmc value; Menger F. et al., (2000). In summary, high cmc and $\gamma_{cmc}$ was observed for the surfactant (2) while the surfactant (6) showed the least cmc and $\gamma_{cmc}$.

The gemini surfactant ability to lower the surface tension of water ($\pi$cmc), highest surface access ($r_{max}$) at the interface of air-water, as well as nominal surface area per molecule ($A_{min}$) was given in Table 1. The method used to calculate these properties was also given in our previous publication; Hussain S S, Animashaun M A, Kamal M S, Ullah N, Hussein I A, Sultan A S (2016) *Synthesis, Characterization and Surface Properties of Amidosulfobetaine Surfactants Bearing Odd-Number Hydrophobic Tail*. J Surfactants Deterg 19 (2):413-420, incorporated herein by reference in its entirety.

The nominal surface area per molecule decreased by increasing the hydrophobic tail, spacer length and increased by increasing the spacer rigidity. The highest surface access at the air-water interface increased by increasing the hydrophobic tail and spacer length.

As shown herein, the inventors synthesized amido-amine-based cationic gemini surfactants (1)-(6) with excellent yields and at high purity from the commercially available carboxylic acids. These gemini surfactants exhibited excellent short-term and long-term thermal stabilities, impressive surface activities and excellent surface tensions. Thermogravimetric analysis demonstrated excellent thermal stabilities of the synthesized surfactants (1)-(6) with no structural degradation up to 200° C. Moreover, the inventors noticed that the thermal stability increased with increase of the chain length of the surfactants.

Long-term thermal stability was assessed using novel approach based on structure characterization before and after aging. The NMR and FTIR results revealed excellent long-term thermal stability of the gemini surfactants (1)-(6) with no change in the structures even after aging for 10 days at 90° C.

These gemini surfactants show a great potential in lowering the surface tension values with quite low cmc. Gemini surfactant (2) demonstrated the highest cmc and corresponding surface tension values, however, gemini surfactant (6) displayed the least cmc and corresponding surface tension values among all the investigated surfactants.

Surfactants with a trans conformation were found to be predominant as compared to surfactants with a cis conformation. The great tolerance to high temperature and unique surface activities of the synthesized gemini surfactants (1)-(6) permits their use for many oilfield applications.

The invention claimed is:

1. A gemini surfactant, comprising:
a cation part having a structure (I), and
an anion part having a combined charge of −2,

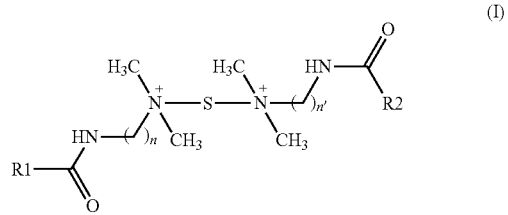

(I)

wherein:
R1 and R2 are $C_8$-$C_{30}$ alkyl or $C_{10}$-$C_{30}$ alkenyl,
S is a $C_4$-$C_8$ alkenylene spacer, and
n and n' are integer values from 2 to 5.

2. The gemini surfactant of claim 1 that is selected from the group consisting of surfactants of formulas (1), (2), (3), and (4):

3. The gemini surfactant of claim 1, wherein S is a linear $C_4$-$C_8$ alkenylene spacer containing at least one cis-double bond.

4. The gemini surfactant of claim 1, wherein S is wherein S is a linear $C_4$-$C_8$ alkenylene spacer containing at least one trans-double bond.

5. The gemini surfactant of claim 2 that has formula (1).

6. The gemini surfactant of claim 2 that has formula (2).

7. The gemini surfactant of claim 2 that has formula (3).

8. The gemini surfactant of claim 2 that has formula (4).

9. A composition comprising one or more of the gemini surfactants of claim 1 and water.

10. The composition of claim 9, further comprising at least one of a monomeric surfactant, a demulsifier, and a coupling agent.

11. A method for increasing a recovery of crude oil or another hydrocarbon from a subterranean hydrocarbon-containing formation or during hydraulic fracturing, comprising:
injecting a composition comprising the gemini surfactant of claim 1 into a subterranean hydrocarbon-containing formation.

12. The method of claim 11, wherein the subterranean hydrocarbon-containing formation is a carbonate reservoir.

13. The method of claim 11, wherein the subterranean hydrocarbon-containing formation is a sandstone reservoir.

14. The method of claim 11, wherein the subterranean hydrocarbon-containing formation is a tight shale reservoir.

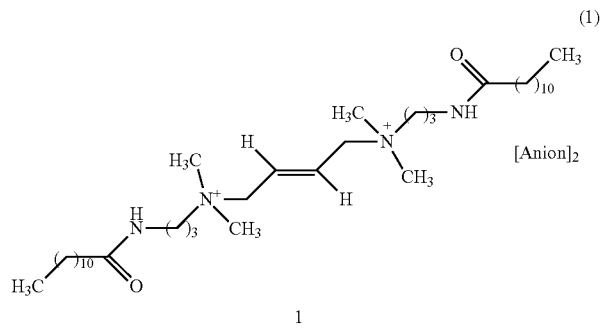

(1)

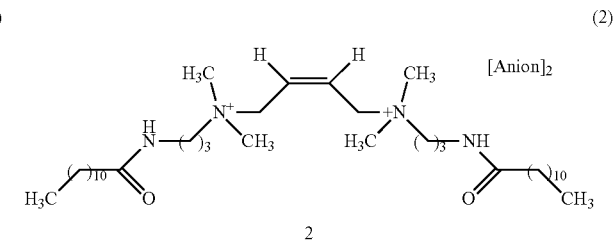

(2)

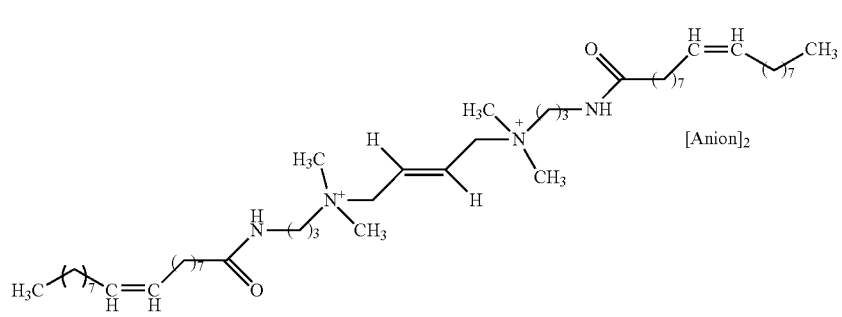

(3)

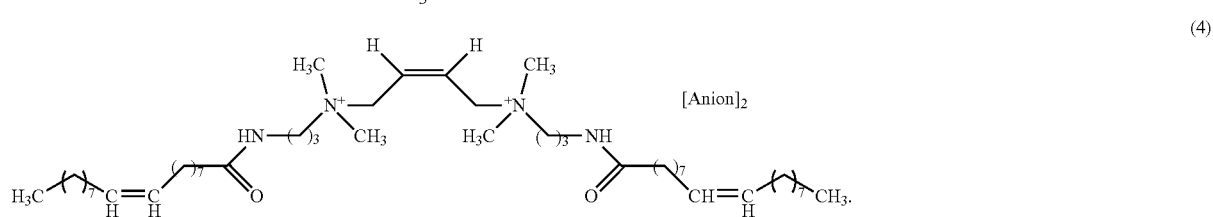

(4)

15. A method of increasing recovery of hydrocarbons from a hydrocarbon-containing subterranean fractured rock formation, comprising:
   forming a composition comprising the gemini surfactant of claim 1 and water, and at least one component selected from the group consisting of a cationic monomer surfactant, a demulsifier, and a coupling agent,
   injecting the composition into the hydrocarbon-containing subterranean fractured rock formation; and
   collecting a hydrocarbon from the hydrocarbon-containing subterranean fractured rock formation.

16. The method of claim 15, where the gemini surfactant is present in the composition at a concentration of 0.001 to 1 wt % based on the total weight of the composition.

17. The method of claim 15, wherein the water is produced water or flowback water.

18. The method of claim 15, wherein the injecting is into a first wellbore connected to the subterranean hydrocarbon-containing fractured rock formation, and
   wherein the collecting is from a second wellbore that is connected to the subterranean hydrocarbon-containing fractured rock formation.

* * * * *